US012678485B2

(12) United States Patent
Bergstein

(10) Patent No.: US 12,678,485 B2
(45) Date of Patent: Jul. 14, 2026

(54) METHODS OF TREATING AN AUTOIMMUNE DISEASE WITH A HUMAN INTERLEUKIN-3 (IL-3)-DIPHTHERIA TOXIN CONJUGATE (DT-IL3)

(71) Applicant: Stemline Therapeutics, Inc., New York, NY (US)

(72) Inventor: Ivan Bergstein, New York, NY (US)

(73) Assignee: Stemline Therapeautics, Inc., New York, NY (US)

( * ) Notice: Subject to any disclaimer, the term of this patent is extended or adjusted under 35 U.S.C. 154(b) by 806 days.

(21) Appl. No.: 17/049,519

(22) PCT Filed: Apr. 26, 2019

(86) PCT No.: PCT/US2019/029363
§ 371 (c)(1),
(2) Date: Oct. 21, 2020

(87) PCT Pub. No.: WO2019/210179
PCT Pub. Date: Oct. 31, 2019

(65) Prior Publication Data
US 2021/0361744 A1     Nov. 25, 2021

Related U.S. Application Data

(60) Provisional application No. 62/663,343, filed on Apr. 27, 2018.

(51) Int. Cl.
*A61K 38/20*     (2006.01)
*A61K 47/68*     (2017.01)
*G01N 33/68*     (2006.01)

(52) U.S. Cl.
CPC ........ *A61K 38/202* (2013.01); *A61K 47/6829* (2017.08); *G01N 33/68* (2013.01); *G01N 2333/523* (2013.01); *G01N 2333/525* (2013.01); *G01N 2333/5412* (2013.01); *G01N 2333/5421* (2013.01); *G01N 2333/57* (2013.01)

(58) Field of Classification Search
None
See application file for complete search history.

(56) References Cited

U.S. PATENT DOCUMENTS

2015/0038679 A1*  2/2015  Nelson ............... A61K 47/6415
                                                          530/351
2016/0024167 A1*  1/2016  Frankel .................. A61K 35/14
                                                          424/85.2

FOREIGN PATENT DOCUMENTS

| | | |
|---|---|---|
| AU | 2013200910 B2 | 6/2015 |
| AU | 2017245391 A1 | 11/2017 |
| WO | 2009100342 A2 | 8/2009 |
| WO | 2011023824 A2 | 3/2011 |

OTHER PUBLICATIONS

Skolnick et al (Trends Biotechnol. Jan. 2000;18(1):34-9) (Year: 2000).*
Burgess et al. (J. Cell Biol. 111:2129-2138, 1990) (Year: 1990).*
Lazar et al. (Mol. Cell. Biol., 8:1247-1252, 1988) (Year: 1998).*
Miosge (Proc Natl Acad Sci U S A. Sep. 15, 2015;112(37):E5189-98) (Year: 2015).*
National Cancer Institute definition of "treatment cycle," downloaded on May 6, 2023 from https://www.cancer.gov/publications/dictionaries/cancer-terms/def/treatment-cycle (Year: 2023).*
Baechler et al (Proc Natl Acad Sci. Mar. 4, 2003;100(5):2610-5) (Year: 2003).*
Van der Fits (J Invest Dermatol 122:51-60, 2004) (Year: 2004).*
Waiker et al (J Am Soc Nephrol. Jan. 2012; 23(1): 13-21) (Year: 2012).*
Mayeux (NeuroRx. Apr. 2004;1(2):182-8) (Year: 2004).*
NCBI GenBank Accession No. AAC08706.1 (submitted Mar. 31, 1998; reference sequence downloaded Feb. 26, 2024 from https://www.ncbi.nlm.nih.gov/protein/AAC08706) (Year: 1998).*
NCBI GenBank Accession No. AAN28949.1 (submitted Aug. 14, 2002; reference sequence downloaded from https://www.ncbi.nlm.nih.gov/protein/AAN28949 on Feb. 26, 2024) (Year: 2002).*
Feng et al., "Association of Increased Interferon-Inducible Gene Expression With Disease Activity and Lupus Nephritis in Patients With Systemic Lupus Erythematosus," Arthritis & Rheumatism, vol. 54, No. 9, pp. 2951-2962 (2006).
Frankel et al., "The AML recombinant toxin, DT388IL3, consisting of a truncated diphtheria toxin (DT388) linked to human interleukin 3 (IL3), shows safety at therapeutically active doses in cynomolgus monkeys," Blood, The American Society of Hematology, vol. 102, No. 11. abstract, p. 386a (2003).
International Search Report and Written Opinion issued in PCT/US2019/029363, dated Aug. 9, 2019; 17 pages.
Li et al., "Disease-Associated Plasmacytoid Dendritic Cells," Frontiers in Immunology, vol. 8, pp. 1-12 (2017).
Palli et al., "Type I Interferon Signature in Primary Antiphospholipid Syndrome: Clinical and Laboratory Associations" Frontiers in Immunology vol. 10, pp. 1-7 (2019).
Prescribing Information for ARCALYSTTM (rilonacept), pp. 1-43, (2008).
Nielsen et al., "A Brief History of Protein Sorting Prediction," The Protein Journal (2019) 38: pp. 200-216.

\* cited by examiner

*Primary Examiner* — Brian Gangle
*Assistant Examiner* — Andrea K Mccollum
(74) *Attorney, Agent, or Firm* — McNeill PLLC

(57)     ABSTRACT

The present disclosure provides, in part, a method of treating an autoimmune disease in a subject by reducing the number of pDCs through administration of a human interleukin-3 (IL-3)-diphtheria toxin conjugate (DT-IL3). The disclosure also generally relates to methods of monitoring the effectiveness of therapy in subjects receiving DT-IL3 for treating an autoimmune disease, and methods of determining continuing treatment of subjects receiving DT-IL3 for treating an autoimmune disease. The disclosure also provides pharmaceutical compositions of DT-IL3 for use in such methods.

16 Claims, 6 Drawing Sheets

Specification includes a Sequence Listing.

| Sample | CD123 MFI |
|--------|-----------|
| HV | 16501 |
| SSc1 | 18852 |
| SSc2 | 17886 |

IL-6

IL-6

SEQUENCE LISTING

<160> NUMBER OF SEQ ID NOS: 3

<210> SEQ ID NO 1
<211> LENGTH: 560
<212> TYPE: PRT
<213> ORGANISM: Corynebacterium diphtheriae

<400> SEQUENCE: 1

```
Met Ser Arg Lys Leu Phe Ala Ser Ile Leu Ile Gly Ala Leu Leu Gly
1               5                   10                  15

Ile Gly Ala Pro Pro Ser Ala His Ala Gly Ala Asp Asp Val Val Asp
            20                  25                  30

Ser Ser Lys Ser Phe Val Met Glu Asn Phe Ser Ser Tyr His Gly Thr
        35                  40                  45

Lys Pro Gly Tyr Val Asp Ser Ile Gln Lys Gly Ile Gln Lys Pro Lys
    50                  55                  60

Ser Gly Thr Gln Gly Asn Tyr Asp Asp Asp Trp Lys Gly Phe Tyr Ser
65                  70                  75                  80

Thr Asp Asn Lys Tyr Asp Ala Ala Gly Tyr Ser Val Asp Asn Glu Asn
                85                  90                  95

Pro Leu Ser Gly Lys Ala Gly Gly Val Val Lys Val Thr Tyr Pro Gly
            100                 105                 110

Leu Thr Lys Val Leu Ala Leu Lys Val Asp Asn Ala Glu Thr Ile Lys
        115                 120                 125

Lys Glu Leu Gly Leu Ser Leu Thr Glu Pro Leu Met Glu Gln Val Gly
    130                 135                 140
```

-continued

```
Thr Glu Glu Phe Ile Lys Arg Phe Gly Asp Gly Ala Ser Arg Val Val
145             150             155             160

Leu Ser Leu Pro Phe Ala Glu Gly Ser Ser Ser Val Glu Tyr Ile Asn
            165             170             175

Asn Trp Glu Gln Ala Lys Ala Leu Ser Val Glu Leu Glu Ile Asn Phe
        180             185             190

Glu Thr Arg Gly Lys Arg Gly Gln Asp Ala Met Tyr Glu Tyr Met Ala
        195             200             205

Gln Ala Cys Ala Gly Asn Arg Val Arg Arg Ser Val Gly Ser Ser Leu
    210             215             220

Ser Cys Ile Asn Leu Asp Trp Asp Val Ile Arg Asp Lys Thr Lys Thr
225             230             235             240

Lys Ile Glu Ser Leu Lys Glu His Gly Pro Ile Lys Asn Lys Met Ser
            245             250             255

Glu Ser Pro Asn Lys Thr Val Ser Glu Glu Lys Ala Lys Gln Tyr Leu
            260             265             270

Glu Glu Phe His Gln Thr Ala Leu Glu His Pro Glu Leu Ser Glu Leu
            275             280             285

Lys Thr Val Thr Gly Thr Asn Pro Val Phe Ala Gly Ala Asn Tyr Ala
    290             295             300

Ala Trp Ala Val Asn Val Ala Gln Val Ile Asp Ser Glu Thr Ala Asp
305             310             315             320

Asn Leu Glu Lys Thr Thr Ala Ala Leu Ser Ile Leu Pro Gly Ile Gly
            325             330             335

Ser Val Met Gly Ile Ala Asp Gly Ala Val His His Asn Thr Glu Glu
            340             345             350

Ile Val Ala Gln Ser Ile Ala Leu Ser Ser Leu Met Val Ala Gln Ala
            355             360             365

Ile Pro Leu Val Gly Glu Leu Val Asp Ile Gly Phe Ala Ala Tyr Asn
    370             375             380

Phe Val Glu Ser Ile Ile Asn Leu Phe Gln Val Val His Asn Ser Tyr
385             390             395             400

Asn Arg Pro Ala Tyr Ser Pro Gly His Lys Thr Gln Pro Phe Leu His
            405             410             415

Asp Gly Tyr Ala Val Ser Trp Asn Thr Val Glu Asp Ser Ile Ile Arg
            420             425             430

Thr Gly Phe Gln Gly Glu Ser Gly His Asp Ile Lys Ile Thr Ala Glu
            435             440             445

Asn Thr Pro Leu Pro Ile Ala Gly Val Leu Leu Pro Thr Ile Pro Gly
    450             455             460

Lys Leu Asp Val Asn Lys Ser Lys Thr His Ile Ser Val Asn Gly Arg
465             470             475             480

Lys Ile Arg Met Arg Cys Arg Ala Ile Asp Gly Asp Val Thr Phe Cys
            485             490             495

Arg Pro Lys Ser Pro Val Tyr Val Gly Asn Gly Val His Ala Asn Leu
            500             505             510

His Val Ala Phe His Arg Ser Ser Ser Glu Lys Ile His Ser Asn Glu
            515             520             525

Ile Ser Ser Asp Ser Ile Gly Val Leu Gly Tyr Gln Lys Thr Val Asp
    530             535             540

His Thr Lys Val Asn Ser Lys Leu Ser Leu Phe Phe Glu Ile Lys Ser
545             550             555             560
```

```
<210> SEQ ID NO 2
<211> LENGTH: 152
<212> TYPE: PRT
<213> ORGANISM: Homo sapiens

<400> SEQUENCE: 2

Met Ser Arg Leu Pro Val Leu Leu Leu Leu Gln Leu Leu Val Arg Pro
1               5                   10                  15

Gly Leu Gln Ala Pro Met Thr Gln Thr Thr Ser Leu Lys Thr Ser Trp
            20                  25                  30

Val Asn Cys Ser Asn Met Ile Asp Glu Ile Ile Thr His Leu Lys Gln
        35                  40                  45

Pro Pro Leu Pro Leu Leu Asp Phe Asn Asn Leu Asn Gly Glu Asp Gln
    50                  55                  60

Asp Ile Leu Met Glu Asn Asn Leu Arg Arg Pro Asn Leu Glu Ala Phe
65                  70                  75                  80

Asn Arg Ala Val Lys Ser Leu Gln Asn Ala Ser Ala Ile Glu Ser Ile
                85                  90                  95

Leu Lys Asn Leu Leu Pro Cys Leu Pro Leu Ala Thr Ala Ala Pro Thr
            100                 105                 110

Arg His Pro Ile His Ile Lys Asp Gly Asp Trp Asn Glu Phe Arg Arg
        115                 120                 125

Lys Leu Thr Phe Tyr Leu Lys Thr Leu Glu Asn Ala Gln Ala Gln Gln
    130                 135                 140

Thr Thr Leu Ser Leu Ala Ile Phe
145                 150

<210> SEQ ID NO 3
<211> LENGTH: 388
<212> TYPE: PRT
<213> ORGANISM: Corynebacterium diphtheriae

<400> SEQUENCE: 3

Gly Ala Asp Asp Val Val Asp Ser Ser Lys Ser Phe Val Met Glu Asn
1               5                   10                  15

Phe Ser Ser Tyr His Gly Thr Lys Pro Gly Tyr Val Asp Ser Ile Gln
            20                  25                  30

Lys Gly Ile Gln Lys Pro Lys Ser Gly Thr Gln Gly Asn Tyr Asp Asp
        35                  40                  45

Asp Trp Lys Gly Phe Tyr Ser Thr Asp Asn Lys Tyr Asp Ala Ala Gly
    50                  55                  60

Tyr Ser Val Asp Asn Glu Asn Pro Leu Ser Gly Lys Ala Gly Gly Val
65                  70                  75                  80

Val Lys Val Thr Tyr Pro Gly Leu Thr Lys Val Leu Ala Leu Lys Val
                85                  90                  95

Asp Asn Ala Glu Thr Ile Lys Lys Glu Leu Gly Leu Ser Leu Thr Glu
            100                 105                 110

Pro Leu Met Glu Gln Val Gly Thr Glu Glu Phe Ile Lys Arg Phe Gly
        115                 120                 125

Asp Gly Ala Ser Arg Val Val Leu Ser Leu Pro Phe Ala Glu Gly Ser
    130                 135                 140

Ser Ser Val Glu Tyr Ile Asn Asn Trp Glu Gln Ala Lys Ala Leu Ser
145                 150                 155                 160

Val Glu Leu Glu Ile Asn Phe Glu Thr Arg Gly Lys Arg Gly Gln Asp
            165                 170                 175
```

-continued

```
Ala Met Tyr Glu Tyr Met Ala Gln Ala Cys Ala Gly Asn Arg Val Arg
            180             185             190

Arg Ser Val Gly Ser Ser Leu Ser Cys Ile Asn Leu Asp Trp Asp Val
            195             200             205

Ile Arg Asp Lys Thr Lys Thr Lys Ile Glu Ser Leu Lys Glu His Gly
        210             215             220

Pro Ile Lys Asn Lys Met Ser Glu Ser Pro Asn Lys Thr Val Ser Glu
225             230             235             240

Glu Lys Ala Lys Gln Tyr Leu Glu Glu Phe His Gln Thr Ala Leu Glu
            245             250             255

His Pro Glu Leu Ser Glu Leu Lys Thr Val Thr Gly Thr Asn Pro Val
            260             265             270

Phe Ala Gly Ala Asn Tyr Ala Ala Trp Ala Val Asn Val Ala Gln Val
            275             280             285

Ile Asp Ser Glu Thr Ala Asp Asn Leu Glu Lys Thr Thr Ala Ala Leu
        290             295             300

Ser Ile Leu Pro Gly Ile Gly Ser Val Met Gly Ile Ala Asp Gly Ala
305             310             315             320

Val His His Asn Thr Glu Glu Ile Val Ala Gln Ser Ile Ala Leu Ser
            325             330             335

Ser Leu Met Val Ala Gln Ala Ile Pro Leu Val Gly Glu Leu Val Asp
            340             345             350

Ile Gly Phe Ala Ala Tyr Asn Phe Val Glu Ser Ile Ile Asn Leu Phe
            355             360             365

Gln Val Val His Asn Ser Tyr Asn Arg Pro Ala Tyr Ser Pro Gly His
    370             375             380

Lys Thr Arg Pro
385
```

METHODS OF TREATING AN AUTOIMMUNE DISEASE WITH A HUMAN INTERLEUKIN-3 (IL-3)-DIPHTHERIA TOXIN CONJUGATE (DT-IL3)

CROSS REFERENCE TO RELATED APPLICATIONS

This application is a national phase entry pursuant to 35 U.S.C. (371 of International Application No. PCT/US2019/029363, filed Apr. 26, 2019, which claims priority to U.S. Provisional Application Ser. No. 62/663,343, filed Apr. 27, 2018, the contents of both of which are hereby incorporated by reference in their entirety

SEQUENCE LISTING

The present application is filed with a Sequence Listing in electronic format. The Sequence Listing is provided as a file entitled "2020-09-24 SeqList ST25" created on Sep. 24, 2020, which is 10,019 bytes in size. The information in the electronic format of the sequence listing is incorporated herein by reference in its entirety.

FIELD OF THE INVENTION

The present disclosure relates to the fields of molecular biology and immunology. In particular, the present disclosure provides methods of treating an autoimmune disease by reducing the number of plasmacytoid dendritic cells (pDCs) in a subject using a human interleukin-3 (IL-3)-diphtheria toxin conjugate (DT-IL3).

BACKGROUND OF THE INVENTION

Autoimmune diseases are caused by immune cells attacking the host tissues they are supposed to protect. Autoimmune disease contributes substantially to morbidity, mortality, and health care cost each year. See, e.g., Rosenblum, et al. *Science translational medicine*. (2012); 4(125):125sr1.

There is an on-going and urgent need to develop new approaches for the treatment of autoimmune diseases, including, for example, psoriasis, lupus, and systemic sclerosis (SSc). Provided herein are methods of treating an autoimmune disease, methods of monitoring the effectiveness of said treatment, and methods of monitoring plasmacytoid dendritic cells (pDCs) as an indicator for continuing treatment of an autoimmune disease.

SUMMARY

The present disclosure, in part, provides methods of treating an autoimmune disease, methods of monitoring the effectiveness of said treatment, and methods of monitoring plasmacytoid dendritic cells (pDCs) as an indicator for continuing treatment of an autoimmune disease. In one aspect, the present disclosure provides methods of treating an autoimmune disease (e.g., lupus (e.g., systemic lupus erythematosus, cutaneous lupus), Sjogren's syndrome, inflammatory arthritis, systemic sclerosis (SSc), morphea, psoriasis, lichen planus, dermatomyositis, lichen sclerosus, or cutaneous graft-versus-host disease (GVHD)) in a subject (e.g., a human) in need thereof by reducing (e.g., depleting, inhibiting, and/or killing) the number of pDCs in the subject by administering a therapeutically effective amount of a human interleukin-3 (IL-3)-diphtheria toxin conjugate (DT-IL3) to the subject. The present invention also provides pharmaceutical compositions of DT-IL3 for use in accordance with the aforementioned methods.

In one aspect, the present disclosure provides a method of treating an autoimmune disease in a human subject by reducing the number of pDCs in the subject by administering a therapeutically effective amount of DT-IL3 to the subject. In another aspect, the present disclosure provides DT-IL3 for use in a method of treating an autoimmune disease in a human subject by reducing the number of pDCs in the subject by administering a therapeutically effective amount of DT-IL3 to the subject. In certain embodiments, the number of pDCs in the subject is reduced by about 20% to about 95%. In certain embodiments, the reduction in the number of pDCs in the subject is DT-IL3 dose-dependent.

In certain embodiments, the reduction in the number of pDCs is accomplished through selective killing of pDCs by the administered DT-IL3. In certain embodiments, the administration of a DT-IL3 does not affect the number of T cells or B cells in the subject. In certain embodiments, the treated autoimmune disease is lupus (e.g., systemic lupus erythematosus, cutaneous lupus), Sjogren's syndrome, inflammatory arthritis, SSc (e.g., limited SSc, diffuse SSc, early-onset SSc, or late-onset SSc), morphea, psoriasis, lichen planus, dermatomyositis, lichen sclerosus, or cutaneous graft-versus-host disease (GVHD). In a specific embodiment, the treated autoimmune disease is SSc. In certain embodiments, administration of a DT-IL3 to a patient diagnosed with SSc prevents progression of the patient's condition to pulmonary fibrosis and/or pulmonary arterial hypertension—two serious complications that cause death in patients with SSc.

In certain embodiments, the subject with the autoimmune disease exhibits elevated levels of type I interferons or IFN-$\alpha$ compared to healthy individuals. In certain embodiments, the subject with the autoimmune disease exhibits the presence of a type I interferon (IFN)-inducible gene signature, for example, in the skin. In certain embodiments, the type I IFN-inducible gene signature includes an increased expression compared to healthy individuals of at least one of the following genes: IFI27, IFI30, IFI6, IRF1, IFITM1, IFITM2, IFIT1, CXCL9, CXCL10, RSAD2, IFI44, IFI44L, IFI6, GBP1, MxB, SERPING1, LY6E, XAF3, IFIT2, IFIT3, MxA, and IRF7. In certain embodiments, the subject with the autoimmune disease (e.g., morphea, SSc, (e.g., limited SSc, diffuse SSc, early-onset SSc, or late-onset SSC), psoriasis, systemic lupus erythematosus, or cutaneous lupus) has been determined to have elevated expression of at least one type I IFN-inducible gene selected from, for example, IFI27, IFI30, IFI6, IRF1, IFITM1, IFITM2, IFIT1, CXCL9, CXCL10, RSAD2, IFI44, IFI44L, IFI6, GBP1, MxB, SERPING1, LY6E, XAF3, IFIT2, IFIT3, MxA, and IRF7.

In certain embodiments, treating an autoimmune disease by reducing the number of pDCs results in reduced levels of at least one type I IFN-inducible gene selected from, for example, IFI27, IFI30, IFI6, IRF1, IFITM1, IFITM2, IFIT1, CXCL9, CXCL10, RSAD2, IFI44, IFI44L, IFI6, GBP1, MxB, SERPING1, LY6E, XAF3, IFIT2, IFIT3, MxA, and IRF7. In certain embodiments, the reduction in the number of pDCs obtained through the method of treating the autoimmune disease results in amelioration of disease symptoms or reduction in disease indicated by improvement in a disease score (e.g., Modified Rodnan Skin Score; mRSS). In certain embodiments, the resulting reduction in the number of pDCs accomplished by administration of a DT-TL3 results in an amelioration of SSc symptoms or a reduction in SSc, including for example, but not limited to, reduced skin thickness, reduced collagen content, reduced levels of α-smooth muscle actin positive cells, reduced levels of fibroblast activation, and reduced levels of type I IFN-inducible genes.

In certain embodiments of the aforementioned methods of treatment, the DT-IL3 is administered at a dose in the range of about 1 μg/kg to about 100 μg/kg (e.g., about 5 μg/kg to about 25 μg/kg). In certain embodiments of the aforementioned methods of treatment, administration of the DT-IL3 is repeated by administering the DT-IL3 for treatment cycles of at least three weeks (e.g., 3 weeks, 4 weeks, 5 weeks, 6 weeks, 7 weeks, 8 or more weeks). In certain embodiments of the aforementioned methods of treatment, administration of the DT-IL3 is repeated by administering the DT-IL3 at 1-5 doses per treatment cycle (e.g., 1 dose, 2 doses, 3 doses, 4 doses, 5 doses).

In another aspect, the present disclosure provides a method of using modulation in the levels of a cytokine or chemokine to monitor the effectiveness of a therapeutic treatment of an autoimmune disease in a subject, by a) administering DT-IL3 to the subject; and b) subsequently determining levels of at least one cytokine or chemokine from a sample obtained from the subject. In certain embodiments, the present disclosure provides DT-IL3 for use in a method of using modulation in the levels of a cytokine or chemokine to monitor the effectiveness of a therapeutic treatment of an autoimmune disease in a subject, by a) administering the DT-IL3 to the subject; and b) subsequently determining levels of at least one cytokine or chemokine from a sample obtained from the subject.

In another aspect, the present disclosure provides a method of using modulation in the levels of a type I IFN-inducible gene to monitor the effectiveness of a therapeutic treatment of an autoimmune disease in a subject, by a) administering DT-IL3 to the subject; and b) subsequently determining levels of at least one type I IFN-inducible gene from a sample obtained from the subject. In certain embodiments, the present disclosure provides DT-IL3 for use in a method of using modulation in the levels of a type I IFN-inducible gene to monitor the effectiveness of a therapeutic treatment of an autoimmune disease in a subject, by a) administering the DT-IL3 to the subject; and b) subsequently determining levels of at least one type I IFN-inducible gene from a sample obtained from the subject.

In certain embodiments, the sample used to determine cytokine or chemokine levels is a peripheral blood mononuclear cell sample or a skin biopsy. In certain embodiments, subsequent to the administration of DT-IL3, levels of one or more of the cytokines or chemokines are determined to be reduced. Exemplary cytokines or chemokines that can be measured include, but are not limited to, CXCL4, CXCL9, CXCL10, IFN-α, IL-6, TNF-α, IFN-γ, IL-8, Rantes, MIP1α, MIP1β, and MCP1.

In certain embodiments, the sample used to determine type I IFN-inducible gene levels is a peripheral blood mononuclear cell sample or a skin biopsy. In certain embodiments, subsequent to the administration of DT-IL3, levels of one or more type I IFN-inducible gene are determined to be reduced. Exemplary type I IFN-inducible genes that can be measured include, but are not limited to, IFI27, IFI30, IFI6, IRF1, IFITM1, IFITM2, IFIT1, CXCL9, CXCL10, RSAD2, IFI44, IFI44L, IFI6, GBP1, MxB, SERPING1, LY6E, XAF3, IFIT2, IFIT3, MxA, and IRF7.

In another aspect, the present disclosure provides a method of using, as an indicator for continuing treatment with DT-IL3, modulation in the number of pDCs in a sample (e.g., a peripheral blood mononuclear cell sample and/or skin biopsy) obtained from a subject who has been administered DT-IL3 for treating an autoimmune disease. In certain embodiments, a reduction of at least about 20% in the number of pDCs in the peripheral blood mononuclear cell sample and/or skin biopsy in response to the administration of DT-IL3 is an indicator for the continuing treatment of the subject.

In certain embodiments, modulation in pDC numbers is determined by immunohistochemistry or immunofluorescence of a skin lesion biopsy. In certain embodiments, modulation in pDC number is determined by flow cytometry based quantification of pDCs in a peripheral blood mononuclear cell sample isolated from a blood sample from the subject.

Other objects, features and advantages of the present disclosure will become apparent from the following detailed description. It should be understood, however, that the detailed description and the specific examples, while indicating specific embodiments of the disclosure, are given by way of illustration only, since various changes and modifications within the spirit and scope of the disclosure will become apparent to those skilled in the art from this detailed description.

BRIEF DESCRIPTION OF THE DRAWINGS

FIG. 1A shows average viability of pDCs in PBMC samples from healthy volunteers (n=5) cultured with DT-IL3 (0.01-100 ng/ml)+/−CpG-274 (0.5 mM). pDC viability is shown as a percentage of the control condition (no DT-IL3). FIG. 1B shows viability of pDCs in PBMC samples from individual healthy volunteers (n=5) cultured with DT-IL3 as a percentage of the control condition (CpG-274 only). FIG. 1C shows average viability of pDCs in PBMC samples from SSc patients (n=3) cultured with DT-IL3 (0.01-100 ng/ml)+/−CpG-274 (0.5 mM). pDC viability is shown as a percentage of the control condition (no DT-IL3, CpG-274 only). FIG. 1D shows viability of pDCs in PBMC samples from individual SSc patients (n=3) cultured with DT-IL3 as a percentage of the control condition (CpG-274 only). FIG. 1E shows viability of B cells and T cells exposed to increasing doses of DT-IL3.

FIG. 3A shows absolute quantification of IFN-α secretion as a function of DT-IL3 concentration. FIG. 3B shows IFN-α secretion in CpG-stimulated PBMCs treated with or without 100 ng/ml DT-IL3 as a percentage of control cells not exposed to DT-IL3. FIG. 3C shows absolute quantification of IL-6 secretion as a function of DT-IL3 concentration. FIG. 3D shows IL-6 secretion in CpG-stimulated PBMCs treated with or without 100 ng/ml DT-IL3 as a percentage of control cells not exposed to DT-IL3.

DESCRIPTION OF THE SEQUENCES

Figure 1A:
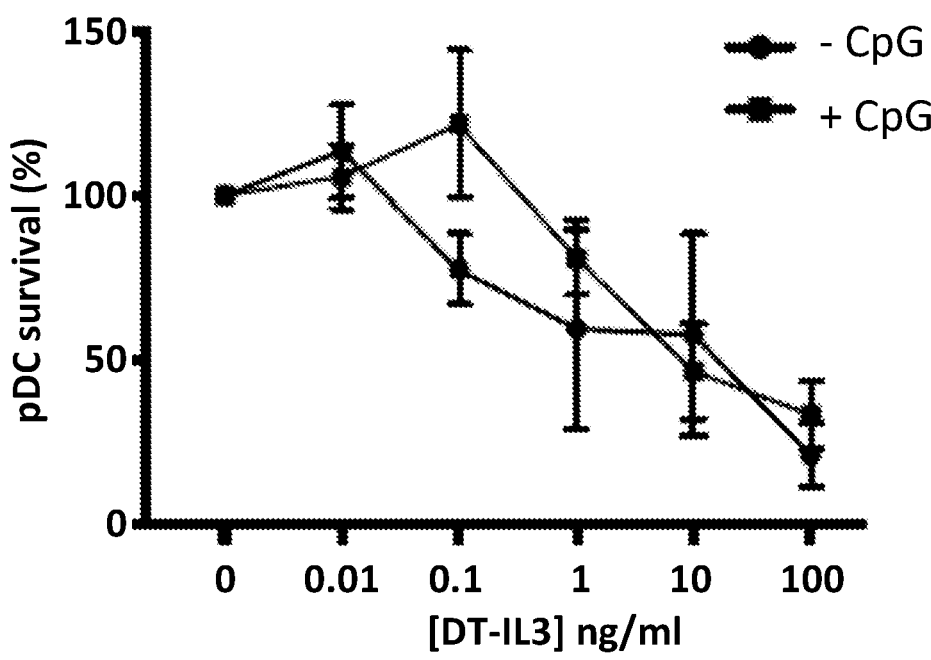
FIGS. 1A-E provide a series of graphs showing cellular viability upon incubation of CpG-274-stimulated PBMCs obtained from healthy volunteers and SSc patients with increasing doses of DT-IL3.

Table 1 provides a listing of certain sequences referenced herein.

5

TABLE 1

| Description of the Sequences | | |
|---|---|---|
| Description | Sequences | SEQ ID NO. |
| DT (diphtheria toxin) | MSRKLFASIL IGALLGIGAP PSAHAGADDV VDSSKSFVME NFSSYHGTKP GYVDSIQKGI QKPKSGTQGN YDDDWKGFYS TDNKYDAAGY SVDNENPLSG KAGGVVKVTY PGLTKVLALK VDNAETIKKE LGLSLTEPLM EQVGTEEFIK RFGDGASRVV LSLPFAEGSS SVEYINNWEQ AKALSVELEI NFETRGKRGQ DAMYEYMAQA CAGNRVRRSV GSSLSCINLD WDVIRDKTKT KIESLKEHGP IKNKMSESPN KTVSEEKAKQ YLEEFHQTAL EHPELSELKT VTGTNPVFAG ANYAAWAVNV AQVIDSETAD NLEKTTAALS ILPGIGSVMG IADGAVHHNT EEIVAQSIAL SSLMVAQAIP LVGELVDIGF AAYNFVESII NLFQVVHNSY NRPAYSPGHK TQPFLHDGYA VSWNTVEDSI IRTGFQGESG HDIKITAENT PLPIAGVLLP TIPGKLDVNK SKTHISVNGR KIRMRCRAID GDVTFCRPKS PVYVGNGVHA NLHVAFHRSS SEKIHSNEIS SDSIGVLGYQ KTVDHTKVNS KLSLFFEIKS | 1 |
| Human IL-3 | MSRLPVLLLL QLLVRPGLQA PMTQTTSLKT SWVNCSNMID EIITHLKQPP LPLLDFNNLN GEDQDILMEN NLRRPNLEAF NRAVKSLQNA SAIESILKNL LPCLPLATAA PTRHPIHIKD GDWNEFRRKL TFYLKTLENA QAQQTTLSLA IF | 2 |
| DT Fragment | GADDVVDSSK SFVMENFSSY HGTKPGYVDS IQKGIQKPKS GTQGNYDDDW KGFYSTDNKY DAAGYSVDNE NPLSGKAGGV VKVTYPGLTK VLALKVDNAE TIKKELGLSL TEPLMEQVGT EEFIKRFGDG ASRVVLSLPF AEGSSSVEYI NNWEQAKALS VELEINFETR GKRGQDAMYE YMAQACAGNR VRRSVGSSLS CINLDWDVIR DKTKTKIESL KEHGPIKNKM SESPNKTVSE EKAKQYLEEF HQTALEHPEL SELKTVTGTN PVFAGANYAA WAVNVAQVID SETADNLEKT TAALSILPGI GSVMGIADGA VHHNTEEIVA QSIALSSLMV AQAIPLVGEL VDIGFAAYNF VESIINLFQV VHNSYNRPAY SPGHKTRP | 3 |

DETAILED DESCRIPTION

The present disclosure is based, in part, upon advancements in understanding the molecular pathways that contribute to the pathogenesis of lupus (e.g., SLE), systemic sclerosis and other autoimmune diseases. The present disclosure provides methods of treating an autoimmune disease in a subject, methods of monitoring the effectiveness of said treatment, and methods of determining continuing treatment of an autoimmune disease. In particular, the present disclosure provides methods of treating an autoimmune disease (e.g., lupus (e.g., systemic lupus erythematosus, cutaneous lupus), Sjogren's syndrome, inflammatory arthritis, systemic sclerosis (SSc), morphea, psoriasis, lichen planus, dermatomyositis, lichen sclerosus, or cutaneous graft-versus-host disease (GVHD)) in a subject (e.g., a human) in need thereof by selective reduction, depletion, inhibition, and/or killing of the subject's plasmacytoid dendritic cell (pDC) population by administering a DT-IL3 to the subject. The present invention also provides pharmaceutical compositions of a DT-IL3 for use in accordance with the aforementioned methods. These and other aspects of the disclosure are set out in detail below.

Definitions

The following definitions are included for the purpose of understanding the present subject matter and for constructing the appended patent claims.

Throughout the application, where compositions are described as having, including, or comprising specific components, or where processes are described as having, including, or comprising specific process steps, it is contemplated that compositions of the present teachings also consist essentially of, or consist of, the recited components, and that the processes of the present teachings also consist essentially of, or consist of, the recited process steps.

In the application, where an element or component is said to be included in and/or selected from a list of recited elements or components, it should be understood that the element or component can be any one of the recited elements or components, or the element or component can be selected from a group consisting of two or more of the recited elements or components. Further, it should be understood that elements and/or features of a composition, an apparatus, or a method described herein can be combined in a variety of ways without departing from the spirit and scope of the present teachings, whether explicit or implicit herein.

It should be understood that the expression "at least one of" includes individually each of the recited objects after the expression and the various combinations of two or more of the recited objects unless otherwise understood from the context and use.

The use of the term "include," "includes," "including," "have," "has," "having," "contain," "contains," or "containing," including grammatical equivalents thereof, should be understood generally as open-ended and non-limiting, for example, not excluding additional unrecited elements or steps, unless otherwise specifically stated or understood from the context. The use of any and all examples, or exemplary language herein, for example, "such as," "including," or "for example," is intended merely to better illustrate the present teachings and does not pose a limitation on the scope of the invention unless claimed. No language in the specification should be construed as indicating any non-claimed element as essential to the practice of the present teachings.

The use of the singular herein, for example, "a," "an," or "the," includes the plural (and vice versa) unless specifically stated otherwise.

It should be understood that the order of steps or order for performing certain actions is immaterial so long as the present teachings remain operable. Moreover, two or more steps or actions can be conducted simultaneously.

At various places in the present specification, values are disclosed in groups or in ranges. It is to be understood that such range formats are used merely for convenience and brevity and should be interpreted flexibly. It is specifically intended that the description include each and every individual subcombination of the members of such groups and ranges and any combination of the various endpoints of such groups or ranges. For example, an integer in the range of 0 to 40 is specifically intended to individually disclose 0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, and 40, and an integer in the range of 1 to 20 is specifically intended to individually disclose 1, 2, 3, 4, 5, 6, 7, 8, 9, 10, 11, 12, 13, 14, 15, 16, 17, 18, 19, and 20.

As used herein, the term "agent" refers to any molecule, compound, and/or substance for use in the prevention, treatment, management and/or diagnosis of an autoimmune disease, including the diphtheria toxin-interleukin-3 conjugate of the invention.

As used herein, the term "conjugate of the invention" refers to interleukin-3 or a portion, analog or derivative thereof that binds to the interleukin-3 receptor or subunit thereof conjugated to diphtheria toxin, a portion thereof or an analog thereof. Unless otherwise indicated, the terms "compound of the invention" and "composition of the invention" are used as alternatives for the term "conjugate of the invention."

As used herein, the term "number" as used in the context of the amount of a particular cell population or cells, refers to the frequency, quantity, percentage, relative amount, or number of the particular cell population or cells.

As used herein, the terms "about" or "approximately," unless otherwise indicated, refer to a value that is no more than 10% above or below the value being modified by the term.

As used herein, the term "therapeutic agent" refers to any molecule, compound, and/or substance that is used for the purpose of treating and/or managing a disease or disorder. Examples of therapeutic agents include, but are not limited to, proteins, immunoglobulins (e.g., multi-specific Igs, single chain Igs, Ig fragments, polyclonal antibodies and their fragments, monoclonal antibodies and their fragments), peptides (e.g., peptide receptors, selectins), binding proteins, biologics, chemospecific agents, chemotoxic agents (e.g., anti-cancer agents), anti-inflammatory agents, proliferation-based therapy, radiation, chemotherapy, anti-angiogenic agents, and small molecule drugs.

As used herein, the term "effective amount" or "amount sufficient" refers to the amount of a therapeutic composition or therapy that is sufficient to result in the prevention of the development, recurrence, or onset of a disease or disorder (e.g., an autoimmune disease or disorder, for example, lupus, SSc, or psoriasis) and one or more symptoms thereof, to reduce the severity or duration of a disease or disorder, to ameliorate one or more symptoms of a disease or disorder, to prevent the advancement of a disease or disorder, to cause regression of a disease or disorder, and/or to enhance or improve the therapeutic effect(s) of another therapy. In an embodiment, the "effective amount" or "therapeutically effective amount" refers to the amount of a composition that is sufficient to effect beneficial or desired results. The therapeutically effective amount may vary depending upon one or more of: the subject and disease condition being treated, the weight and age of the subject, the severity of the disease condition, the manner of administration and the like, which can readily be determined by one of ordinary skill in the art. In a specific embodiment of the invention, a therapeutic composition in an "amount sufficient" refers to the amount of the composition needed to prevent, reduce, or alleviate at least one or more signs or symptoms of an autoimmune disease (e.g., lupus, SSc, psoriasis), and relates to a sufficient amount of the composition to provide the desired effect, e.g., to treat a subject having an autoimmune disease (e.g., lupus, SSc, or psoriasis). The term "effective amount" therefore refers to an amount of a composition that is sufficient to promote a particular effect when administered to a typical subject, such as one who has or is at risk for an autoimmune disease (e.g., lupus, SSc, or psoriasis). An effective amount would also include an amount sufficient to delay the development of a symptom of the disease, alter the course of a symptom of the disease (for example, but not limited to, slow the progression of a symptom of the disease), or reverse a symptom of the disease. It is understood that for any given case, an appropriate "effective amount" can be determined by one of ordinary skill in the art using routine experimentation.

The terms "subject" and "patient" are used interchangeably herein. The subject treated by the presently disclosed methods in their many embodiments is desirably a human subject, although it is to be understood that the methods described herein are effective with respect to all vertebrate species which are intended to be included in the term "subject." Accordingly, a "subject" can include a human subject for medical purposes, such as for the treatment of an existing condition or disease or the prophylactic treatment for preventing the onset of a condition or disease, or an animal subject for medical, veterinary purposes, or developmental purposes. Suitable animal subjects include mammals including, but not limited to, primates, humans, monkeys, apes, and the like; bovines, e.g., cattle, oxen, and the like; ovines, e.g., sheep and the like; caprines, e.g., goats and the like; porcines, e.g., pigs, hogs, and the like; equines, e.g., horses, donkeys, zebras, and the like; felines, including wild and domestic cats; canines, including dogs; lagomorphs, including rabbits, hares, and the like; and rodents, including mice, rats, and the like. An animal may be a transgenic animal. In certain embodiments, the subject is a human such as an infant, a juvenile, or an adult. Further, a "subject" can include a patient afflicted with or suspected of being afflicted with a condition or disease (e.g., an autoimmune disease, for example but not limited to, lupus (e.g., systemic lupus erythematosus, cutaneous lupus), Sjogren's syndrome, inflammatory arthritis, systemic sclerosis (SSc), morphea, psoriasis, lichen planus, dermatomyositis, lichen sclerosus, or cutaneous graft-versus-host disease (GVHD)).

As used herein, the terms "treat," "treatment," and "treating" in the context of the administration of a therapeutic composition to a subject refer to the reversing, reduction or inhibition of the progression and/or duration of the disease, preventing or reducing the likelihood of the disease, reduction or amelioration of the severity, and/or the amelioration of one or more symptoms of the disease, disorder, or condition to which such term applies resulting from the administration of one or more therapies. In certain embodiments, the treatment reduces the number of plasmacytoid dendritic cells of the subject. For example, the treatment can reduce the number of plasmacytoid dendritic cells of the subject by at least 5%, 10%, 15%, 20%, 25%, 30%, 33%, 35%, 40%, 45%, 50%, 55%, 60%, 70%, 75%, 80%, 85%, 90%, 91%, 92%, 93%, 94%, 95%, 96%, 97%, 98%, 99% or more as compared to the number of plasmacytoid dendritic cells in a subject before undergoing treatment or in a subject who does not undergo treatment.

As used herein, the terms "manage," "managing," and "management" in the context of the administration of a therapy to a subject refer to the beneficial effects that a subject derives from a therapy (e.g., a prophylactic or therapeutic composition) or a combination of therapies, while not resulting in a cure of the disease or disorder. In certain embodiments, a subject is administered one or more therapies (e.g., one or more prophylactic or therapeutic compositions) to "manage" an autoimmune disease (for example, but not limited to, lupus (e.g., systemic lupus erythematosus, cutaneous lupus), Sjogren's syndrome, inflammatory arthritis, systemic sclerosis (SSc), morphea, psoriasis, lichen planus, dermatomyositis, lichen sclerosus, or cutaneous graft-versus-host disease (GVHD)) so as to prevent the progression or worsening of the condition.

As used herein, the terms "prevent," "preventing" and "prevention" in the context of the administration of a therapy to a subject refer to the prevention or inhibition of the recurrence, onset, and/or development of a disease or disorder, or a symptom thereof in a subject resulting from the administration of a therapy (e.g., a prophylactic or therapeutic agent), or a combination of therapies (e.g., a combination of prophylactic or therapeutic agents). In certain embodiments, such terms refer to one, two, three, or more results following the administration of one or more therapies: (1) a delay in the development of a symptom of the disease, (2) an alteration of the course of a symptom of the disease (for example, but not limited to, slowing the progression of a symptom of the disease), (3) a reverse of a symptom of the disease, (4) a decrease in the recurrence rate of the disease, (5) an increase in the time to recurrence of the disease, (6) an increase in the disease-free, relapse-free, progression-free, and/or overall survival of the patient, and (7) an amelioration of disease-related symptoms and/or quality of life. In certain embodiments, such terms refer to a reduction in mortality and/or an increase in survival rate of a patient population. In further embodiments, such terms refer to an increase or enhancement in the quality of life of a patient population. In certain embodiments, such terms refer to a decrease in hospitalization rate of a patient population and/or a decrease in hospitalization length for a patient population.

As used herein, the terms "therapies" and "therapy" can refer to any method(s), composition(s), and/or agent(s) that can be used in the prevention, treatment and/or management of a disease, disorder or condition, or one or more symptoms thereof. In certain embodiments, the terms "therapy" and "therapies" refer to steroid therapy, physical therapy, gene therapy, chemotherapy, small molecule therapy, radioimmunotherapy, toxin therapy, prodrug-activating enzyme therapy, biologic therapy, antibody therapy, surgical therapy, hormone therapy, immunotherapy, anti-angiogenic therapy, targeted therapy, epigenetic therapy, demethylation therapy, histone deacetylase inhibitor therapy, differentiation therapy, radiation therapy, or a combination of the foregoing and/or other therapies useful in the prevention, management and/or treatment of a disease, disorder or condition, or one or more symptoms thereof.

As used herein, the terms "administering" and "administered" refer to the delivery of a composition into a subject by a method or route that results in at least partial localization of the composition at a desired site. A composition can be administered by any appropriate route that results in effective treatment in the subject, i.e., administration results in delivery to a desired location in the subject where at least a portion of the composition is delivered to the desired site for a period of time. Modes of administration include injection, infusion, instillation, or ingestion. "Injection" includes, without limitation, intravenous, intramuscular, intraarterial, intrathecal, intraventricular, intracapsular, intraorbital, intracardiac, intradermal, intraperitoneal, transtracheal, subcutaneous, subcuticular, intraarticular, sub capsular, subarachnoid, intraspinal, intracerebro spinal, and intrasternal injection and infusion. In some examples, the route is intravenous.

As used herein, the term "marker" in the context of a cell or tissue (e.g., a normal or cancer cell or tumor) means any antigen, molecule or other chemical or biological entity that is specifically found in or on a tissue that it is desired to identify or identified in or on a particular tissue affected by a disease or disorder. In specific embodiments, the marker is a cell surface antigen that is differentially or preferentially expressed by specific cell types. For example, CD123 (IL-3R alpha chain) is highly expressed on pDCs compared to other blood cell types. As another example, a leukemia cancer stem cell differentially expresses CD123 relative to a normal hematopoietic stem cell.

As used herein, the term "marker phenotype" in the context of a tissue (e.g., a normal or cancer cell or a tumor cell) means any combination of antigens (e.g., receptors, ligands, and other cell surface markers), molecules, or other chemical or biological entities that are specifically found in or on a tissue that it is desired to identify a particular tissue affected by a disease or disorder. In specific embodiments, the marker phenotype is a cell surface phenotype. In accordance with this embodiment, the cell surface phenotype may be determined by detecting the expression of a combination of cell surface antigens. For instance, a non-limiting example of a plasmacytoid dendritic cell surface phenotype is CD14−, CD3−, BDCA4+, CD123+ as well as those that are known in the art.

Methods of Treatment

The present invention provides methods of treating an autoimmune disease in a subject, e.g., a human, by reducing the number of IL-3 receptor expressing cells in the subject in need thereof by administering an effective amount of a DT-IL3 of the invention that is toxic to cells expressing the IL-3 receptor. In certain embodiments, the cells express the alpha subunit of the interleukin-3 receptor. In certain embodiments, the cells express both the alpha and beta subunits of the IL-3 receptor. In certain embodiments, pDCs, which demonstrate high expression of the alpha chain of the IL-3 receptor, are reduced, inhibited, eliminated, or killed by the methods of treatment disclosed herein.

The present disclosure provides therapies which involve administering DT-IL3 and compositions including the DT-IL3 to a subject, e.g., a human subject, for treating an autoimmune disease.

In particular, in one aspect, the present disclosure provides a method of treating an autoimmune disease in a human subject, the method involving reducing the number of pDCs in the subject by administering a therapeutically effective amount of DT-IL3 to the subject. Also provided herein is DT-IL3 for use in a method of treating an autoimmune disease in a human subject. The method involves reducing the number of pDCs in the subject by administering a therapeutically effective amount of the DT-IL3 to the subject. In certain embodiments, the number of pDCs in the subject is reduced by about 20% to about 95% compared to the level before initiation of treatment. For example, in certain embodiments, the number of pDCs in the subject is reduced by about 20%, about 30%, about 40%, about 50%, about 60%, about 70%, about 80%, or about 90% compared to the level before initiation of treatment. In certain embodiments, the reduction in pDCs is based on a comparison to the number of pDCs in a subject before receiving DT-IL3 treatment.

One of skill in the art will appreciate that the cytotoxic activity of DT-IL3 is dependent on the ability of the IL-3 component of the conjugate to bind to the IL-3 receptor on the surface of a targeted cell. As such, the cytotoxic activity of DT-IL3 can be selectively directed to a specific cell population. In certain embodiments, the methods of treating an autoimmune disease (for example, but not limited to, lupus (e.g., systemic lupus erythematosus, cutaneous lupus), Sjogren's syndrome, inflammatory arthritis, SSc, morphea, psoriasis, lichen planus, dermatomyositis, lichen sclerosus, or cutaneous graft-versus-host disease (GVHD)) by the administered DT-IL3 to a subject involves reduction of pDCs by selective killing of pDCs in the subject. For example, in certain embodiments, about 20%, about 30%, about 40%, about 50%, about 60%, about 70%, about 80%, or about 90% of the population of pDCs prior to DT-IL3 administration is killed. In certain embodiments, the administration of a DT-IL3 does not affect the number of T cells or B cells in the subject. In some embodiments, the administration of a DT-IL3 does not affect the number of T cells or B cells in the subject by more than about 1% to about 15%.

Non-limiting examples of autoimmune disease that can be treated by the methods of the invention include adrenergic drug resistance, alopecia areata, ankylosing spondylitis, antiphospholipid syndrome, autoimmune Addison's disease, autoimmune diseases of the adrenal gland, allergic encephalomyelitis, autoimmune hemolytic anemia, autoimmune hepatitis, autoimmune inflammatory eye disease, autoimmune neonatal thrombocytopenia, autoimmune neutropenia, autoimmune oophoritis and orchitis, autoimmune thrombocytopenia, autoimmune thyroiditis, Behcet's disease, bullous pemphigoid, cardiomyopathy, cardiotomy syndrome, celiac sprue-dermatitis, chronic active hepatitis, chronic fatigue immune dysfunction syndrome (CFIDS), chronic inflammatory demyelinating polyneuropathy, Churg-Strauss syndrome, cicatricial pemphigoid, CREST syndrome, cold agglutinin disease, Crohn's disease, dense deposit disease, discoid lupus, essential mixed cryoglobulinemia, fibromyalgia-fibromyositis, glomerulonephritis (e.g., IgA nephropathy), gluten-sensitive enteropathy, Goodpasture's syndrome, Graves' disease, Guillain-Barre, hyperthyroidism (i.e., Hashimoto's thyroiditis), idiopathic pulmonary fibrosis, idiopathic Addison's disease, idiopathic thrombocytopenia purpura (ITP), IgA neuropathy, juvenile arthritis, lichen planus, lupus erythematosus, Meniere's disease, mixed connective tissue disease, multiple sclerosis, Myasthenia Gravis, myocarditis, type 1 or immune-mediated diabetes mellitus, neuritis, other endocrine gland failure, pemphigus vulgaris, pernicious anemia, polyarteritis nodosa, polychondritis, Polyendocrinopathies, polyglandular syndromes, polymyalgia rheumatica, polymyositis and dermatomyositis, post-MI, primary agammaglobulinemia, primary biliary cirrhosis, psoriasis, psoriatic arthritis, Raynaud's phenomenon, relapsing polychondritis, Reiter's syndrome, rheumatic heart disease, rheumatoid arthritis, sarcoidosis, SSc, Sjögren's syndrome, stiff-man syndrome, systemic lupus erythematosus, takayasu arteritis, temporal arteritis/giant cell arteritis, ulcerative colitis, urticaria, uveitis, Uveitis Ophthalmia, vasculitides such as dermatitis herpetiformis vasculitis, vitiligo, and Wegener's granulomatosis.

In certain embodiments, the autoimmune disease treated by methods disclosed herein is lupus (e.g., systemic lupus erythematosus, cutaneous lupus), Sjögren's syndrome, inflammatory arthritis, SSc (e.g., limited SSc, diffuse SSc, early-onset SSc, or late-onset SSc), morphea, psoriasis, lichen planus, dermatomyositis, lichen sclerosus, or GVHD.

For example, in a specific embodiment, the present disclosure provides a method of treating SSc (e.g., limited SSc, diffuse SSc, early-onset SSc, or late-onset SSc) in a human subject. The method involves reducing the number of pDCs in the subject by administering a therapeutically effective amount of DT-IL3 to the subject. In certain embodiments, administration of DT-IL3 to a patient diagnosed with SSc prevents/delays progression of the patient's condition to pulmonary fibrosis and/or pulmonary arterial hypertension—two sometimes lethal complications in patients with SSc.

In another specific embodiment, the present disclosure provides a method of treating morphea in a human subject. The method involves reducing the number of pDCs in the subject by administering a therapeutically effective amount of a DT-IL3 to the subject.

In yet another embodiment, the present disclosure provides a method of treating psoriasis in a human subject. The method involves reducing the number of pDCs in the subject by administering a therapeutically effective amount of a DT-IL3 to the subject.

In yet another embodiment, provided herein is a method of treating lupus (e.g., systemic lupus erythematosus or cutaneous lupus) in a human subject. The method involves reducing the number of pDCs in the subject by administering a therapeutically effective amount of a DT-IL3 to the subject.

The present invention provides treatment (including reducing symptoms and preventing disease progression) of autoimmune diseases or disorders in which pDCs contribute to or are associated with the pathogenesis of the disease. Different autoimmune diseases may present different phenotypes or symptoms. For example, some autoimmune diseases (for example, lichen planus, dermatomyositis, lichen sclerosus, cutaneous GVHD, and cutaneous lupus) share a common pathological feature called "interface dermatitis" (ID) characterized by vacuolar changes (liquefaction) of the basal layer of the epidermis, appearance of apoptotic keratinocytes (Civatte bodies), and infiltration of CD8+ lymphocytes. Furthermore, ID-related diseases, as well as other autoimmune diseases, exhibit a strong activation of the type I interferon (IFN) system, including type I IFN genes and/or type I IFN-induced genes. The present disclosure contemplates treatment of different subpopulations of patients with an autoimmune disease who may manifest different phenotypes, symptoms, and/or molecular signatures, including a type I IFN-inducible gene signature and/or increased expression of type I IFN-inducible genes.

For example, some methods of treatment provided by the present disclosure include treating subjects who exhibit the presence of a type I interferon (IFN)-inducible gene signature in the affected body part (e.g., the skin). In certain embodiments, the type I IFN-inducible gene signature includes an increased expression compared to healthy individuals of at least one of the following genes: ACTA2, AGRN, ANK3, APOBEC3G, APOL1, BRCA1, BST2, CASP10, CCL8, CD38, CD69, $CDCl_2L2$, CEACAM1, cig5, CXCL10, CXCL11, CXCL9, CYP2J2, DEFB1, DRAP1, DUSP5, DYNLT1, EF1830, EF2647, ENDOD1, FAS, FASLG, FGL2, GBP1, GBP2, GCH1, GMPR, GPR15, HSPA1A, HSPA1B, IDO1, IFI16, IFI35, IFI44, IFI44L, IFI6, IFI27, IFIT2, IFIT3, IFIT5, IFITM2, IGFBP4, IL12RB2, IL15, IL15RA, IL18RAP, IL1RN, IL6, IRF2, IRF7, IRS1, ISG15, ISG20, JAK2, KLF5, LAG3, LAMP3, LGALS3BP, LGALS9, LPIN2, LY6E, MCP-3, MICB, MT3, MXA, MXB, NMI, OAS1, OAS2, OASL, PALM2-AKAP2, PGAP1, PLSCR1, PMAIP1, PML, PRF1, PRKD2, RABGAP1L, RBCK1, RGS1, RIN2, RSAD2, SECTM1, SERPING1, SOCS1, SP100, SP110, SRGAP2, STAT1, STAT2, SYNE2, TAP1, TARBP1, TDRD7, TMEM187, TNFSF10, TRAFD1, TRANK1, TREX1, TRIM14, TRIM21, TRIM22, UBE2L6, VAMP5, WARS, XAF1, XAF3.

In certain embodiments, the type I IFN-inducible gene signature includes an increased expression compared to the levels in healthy individuals of at least one of IFI27, IFI30, IFI6, IRF1, IFITM1, IFITM2, IFIT1, CXCL9, CXCL10, RSAD2, IFI44, IFI44L, IFI6, GBP1, MxB, SERPING1, LY6E, XAF3, IFIT2, IFIT3, MxA, and IRF7. For example, in a specific embodiment, the present disclosure provides a method of treating SSc in a human subject by reducing the number of pDCs in the subject by administering a therapeutically effective amount of DT-IL3 to the subject, after a blood or skin biopsy from the subject has been determined to exhibit an increased expression compared to the levels of healthy individuals of at least one of IFI27, IFI30, IFI6, IRF1, IFITM1, IFITM2, IFIT1, CXCL9, CXCL10, RSAD2, IFI44, IFI44L, IFI6, GBP1, MxB, SERPING1, LY6E, XAF3, IFIT2, IFIT3, MxA, and IRF7.

In certain embodiments, the methods of treatment provided by the present disclosure include treating subjects who exhibit elevated levels of type I IFNs compared to healthy individuals. Non-limiting examples of type I IFNs include IFN-α, IFN-β, IFN-κ, IFN-δ, IFN-ε, IFN-τ, IFN-ω, and IFN-ξ. In a specific embodiment, for example, the present disclosure provides a method of treating an autoimmune disease (e.g., SSc) in a human subject by reducing the number of pDCs in the subject by administering a therapeutically effective amount of DT-IL3 to the subject, after a skin biopsy from the subject has been determined to exhibit elevated expression of IFN-α compared to the IFN-α levels of healthy individuals.

In certain embodiments, the subject with the autoimmune disease has been determined to have elevated expression of at least one type I IFN-inducible gene. Non-limiting examples of type I IFN-inducible genes include ACTA2, AGRN, ANK3, APOBEC3G, APOL1, BRCA1, BST2, CASP10, CCL8, CD38, CD69, CDCl2L2, CEACAM1, cig5, CXCL10, CXCL11, CXCL9, CYP2J2, DEFB1, DRAP1, DUSP5, DYNLT1, EF1830, EF2647, ENDOD1, FAS, FASLG, FGL2, GBP1, GBP2, GCH1, GMPR, GPR15, HSPA1A, HSPA1B, IDO1, IFI16, IFI35, IFI44, IFI44L, IFI6, IFI27, IFIT2, IFIT3, IFIT5, IFITM2, IGFBP4, IL12RB2, IL15, IL15RA, IL18RAP, IL1RN, IL6, IRF2, IRF7, IRS1, ISG15, ISG20, JAK2, KLF5, LAG3, LAMP3, LGALS3BP, LGALS9, LPIN2, LY6E, MCP-3, MICB, MT3, MXA, MXB, NMI, OAS1, OAS2, OASL, PALM2-AKAP2, PGAP1, PLSCR1, PMAIP1, PML, PRF1, PRKD2, RABGAP1L, RBCK1, RGS1, RIN2, RSAD2, SECTM1, SERPING1, SOCS1, SP100, SP110, SRGAP2, STAT1, STAT2, SYNE2, TAP1, TARBP1, TDRD7, TMEM187, TNFSF10, TRAFD1, TRANK1, TREX1, TRIM14, TRIM21, TRIM22, UBE2L6, VAMP5, WARS, XAF1, XAF3.

In certain embodiments, non-limiting examples of type I IFN-inducible genes include IFI27, IFI30, IFI6, IRF1, IFITM1, IFITM2, IFIT1, CXCL9, CXCL10, RSAD2, IFI44, IFI44L, IFI6, IFN-α, GBP1, MxB, SERPING1, LY6E, XAF3, IFIT2, IFIT3, MxA, and IRF7. For example, in a specific embodiment, the present disclosure provides a method of treating SSc in a human subject by reducing the number of pDCs in the subject by administering a therapeutically effective amount of DT-IL3 to the subject, after a skin biopsy from the subject has been determined to exhibit an increased expression compared to healthy individuals of at least one of IFI27, IFI30, IFI6, IRF1, IFITM1, IFITM2, IFIT1, CXCL9, CXCL10, RSAD2, IFI44, IFI44L, IFI6, GBP1, MxB, SERPING1, LY6E, XAF3, IFIT2, IFIT3, MxA, and IRF7.

In certain embodiments, methods of treatment provided herein effect reduced levels of at least one type I IFN-inducible gene, reduced levels of at least one type I interferon, or reduction in or loss of the type I IFN-inducible signature in a sample obtained from the treated subject. For example, in certain embodiments, treating the autoimmune disease results in reduced levels of at least one type I IFN-inducible gene (non-limiting examples include IFI27, IFI30, IFI6, IRF1, IFITM1, IFITM2, IFIT1, CXCL9, CXCL10, RSAD2, IFI44, IFI44L, IFI6, IFN-α, GBP1, MxB, SERPING1, LY6E, XAF3, IFIT2, IFIT3, MxA, and IRF7) in a sample obtained from the subject (e.g., blood, skin biopsy).

In general, the skilled artisan will be able to determine the appropriate standard method for measuring expression level of a particular gene or gene product in accordance with the methods of treatment disclosed herein. Standard methods used for assaying the expression level of a gene or gene product include, but are not limited to, quantitative PCR, microarrays, exome sequencing, RNA sequencing, northern blots, immunohistochemistry, enzyme-linked immunosorbent assays (ELISAs), enzyme-linked immunosorbent spot (ELISpot) assays, western blots, antibody arrays, Luminex assays, reverse transcription PCR (RT-PCR), immunofluorescence, flow cytometry, and in situ hybridization.

In certain embodiments, the reduction in the number of pDCs obtained through the methods of treating the autoimmune disease results in amelioration of disease symptoms or reduction in disease. Methods of evaluating autoimmune patients to determine amelioration of disease symptoms or reduction in disease are known by those skilled in the art. For example, amelioration of disease symptoms or reduction in disease may be assessed via a disease score (e.g., mRSS score in SSc). The effects of a therapy can be monitored by continual assessment of a disease score throughout the course of treatment by comparison of the score at a later time point to the score at a prior time point (e.g., before administration of therapy).

In certain embodiments, the reduction in the number of pDCs accomplished through the methods of treatment disclosed herein results in amelioration of disease symptoms or reduction in disease indicated by reduction in the treated subject's disease score (e.g., mRSS score). For example, in a specific embodiment, the present disclosure provides a method of treating SSc in a human subject by reducing the number of pDCs in the subject by administering a therapeutically effective amount of DT-IL3 to the subject, where the reduction in the number of pDCs results in improvement in the treated subject's mRSS score. In certain embodiments, the resulting reduction in the number of pDCs accomplished through the methods of treatment disclosed herein results in, for example, reduced skin thickness, reduced collagen content, reduced levels of α-smooth muscle actin positive cells, reduced levels of fibroblast activation, reduced levels of IFN-inducible genes. In certain embodiments, the present disclosure provides a method of treating SSc in a human subject by reducing the number of pDCs in the subject by administering a therapeutically effective amount of DT-IL3 to the subject, where the reduction in the number of pDCs results in at least one of reduced skin thickness, reduced collagen content, reduced levels of α-smooth muscle actin positive cells, reduced levels of fibroblast activation, and reduced levels of IFN-inducible genes.

Methods of Monitoring

In another aspect, the present disclosure provides a method of using modulation in the levels of a cytokine or chemokine to monitor the effectiveness of a therapeutic treatment of an autoimmune disease in a subject by a) administering DT-IL3 to the subject; and b) subsequently determining levels of at least one cytokine or chemokine from a sample obtained from the subject. The present disclosure also provides DT-IL3 for use in a method of using modulation in the levels of a cytokine or chemokine to monitor the effectiveness of a therapeutic treatment of an autoimmune disease in a subject, by a) administering DT-IL3 to the subject; and b) subsequently determining levels of at least one cytokine or chemokine from a sample obtained from the subject.

In another aspect, the present disclosure provides a method of using modulation in the levels of a type I IFN-inducible gene to monitor the effectiveness of a therapeutic treatment of an autoimmune disease in a subject, by a) administering DT-IL3 to the subject; and b) subsequently determining levels of at least one type I IFN-inducible gene from a sample obtained from the subject. In certain embodiments, the present disclosure provides DT-IL3 for use in a method of using modulation in the levels of a type I IFN-inducible gene to monitor the effectiveness of a therapeutic treatment of an autoimmune disease in a subject by a) administering DT-IL3 to the subject; and b) subsequently determining levels of at least one type I IFN-inducible gene from a sample obtained from the subject.

The levels of a cytokine or chemokine can be assessed at one or more points during the period of treatment. For example, in certain embodiments, the levels of a cytokine or chemokine in a sample from the treated subject is assessed after the first dose of DT-IL3, and/or after the last dose of DT-IL3, per week of the treatment cycle. Similarly, the levels of a type I IFN-inducible gene can be assessed at one or more points during the period of treatment. For example, in certain embodiments, the levels of a type I IFN-inducible gene in a sample from the treated subject is assessed after the first dose of DT-IL3, and/or after the last dose of DT-IL3, per week of the treatment cycle.

In certain embodiments, the sample used to determine cytokine or chemokine levels is a peripheral blood mononuclear cell sample or a skin biopsy. In certain embodiments, the sample used to determine type I IFN-inducible gene levels is a peripheral blood mononuclear cell sample or a skin biopsy. Methods of peripheral blood mononuclear cell isolation are routine are in the art. For example, a common method for PBMC isolation is a method known as Ficoll® or Ficoll-Paque®. See, e.g., Jaatinen T, et al., *Curr Protoc Stem Cell Biol*, (2007); Chapter 2: Unit 2A.1. A skin biopsy is a safe, easy and out-patient procedure of diagnostic and academic relevance. A skilled artisan will be aware that there are various methods of performing a skin biopsy depending on the size of lesion, suspected clinical diagnosis and site of lesion. Non-limiting examples of skin biopsies for use in accordance with the methods disclosed herein include punch biopsies, shave biopsies, saucerization biopsies, wedge biopsies, incisional biopsies, and excisional biopsies.

In certain embodiments, subsequent to the administration of DT-IL3, levels of one or more of the cytokines or chemokines are determined to be reduced. Exemplary cytokines or chemokines that may be measured, include, but are not limited to, CXCL1, CXCL2, CXCL3, CXCL4, CXCL5, CXCL6, CXCL7, CXCL8, CXCL9, CXCL10, CXCL11, CXCL12, CXCL13, CXCL14, CXCL15, CXCL16, CXCL17, CCL1e, CCL2, CCL3, CCL3L1, CCL4, CCL5, CCL6, CCL7, CCL8, CCL9/10, CCL11, CCL12, CCL13, CCL14, CCL15, CCL16, CCL17, CCL18, CCL19, CCL20, CCL21, CCL22, CCL23, CCL24, CCL25, CCL26, CCL27, CCL28, CX3CL1, XCL1, XCL2, IFN-α, IFN-α, IFN-β, IFN-γ, TNF-α, TNF-β, IL-2, IL-3, IL-4, IL-5, IL-6, IL-7, IL-8, IL-9, IL-10, IL-11, IL-12, IL-13, IL-15, IL-19, IL-20, IL-1α, IL-10, IL-1RA, IL-18, TGF-β1, TGF-02, Rantes, MIP1α, MIP1β, GM-CSF, G-CSF, LIF, and MCP1. In certain embodiments, exemplary cytokines or chemokines that may be measured, include, but are not limited to, CXCL4, CXCL9, CXCL10, IFN-α, IL-6, TNF-α, IFN-γ, IL-8, Rantes, MIP1α, MIP1β, and MCP1.

In certain embodiments, subsequent to the administration of DT-IL3, levels of one or more type I IFN-inducible genes are determined to be reduced. Examples of type I IFN-inducible genes include, but are not limited to, the type I IFN-inducible genes enumerated in the Method of Treatment section above. In certain embodiments, exemplary type I IFN-inducible genes that may be measured, include, but are not limited to, IFI27, IFI30, IFI6, IRF1, IFITM1, IFITM2, IFIT1, CXCL9, CXCL10, RSAD2, IFI44, IFI44L, IFI6, GBP1, MxB, SERPING1, LY6E, XAF3, IFIT2, IFIT3, MxA, and IRF7.

In general, the skilled artisan will be able to determine the appropriate standard method for measuring levels of cytokines, chemokines, or type I IFN-inducible genes in accordance with the methods disclosed herein. Standard methods that may be used include, but are not limited to, quantitative PCR, microarrays, exome sequencing, RNA sequencing, northern blots, immunohistochemistry, enzyme-linked immunosorbent assays (ELISAs), enzyme-linked immunosorbent spot (Elispot) assays western blots, antibody arrays, Luminex assays, reverse transcription PCR (RT-PCR), immunofluorescence, flow cytometry, and in situ hybridization.

Methods of Using Modulation in the Number of pDCs as an Indicator for Continuing Treatment In another aspect, the present disclosure provides a method of using modulation in the number of pDCs as an indicator for continuing treatment of an autoimmune disease in a subject with a DT-IL3 by determining the number of pDCs in a peripheral blood mononuclear cell sample and/or skin biopsy obtained from the subject who has been administered DT-IL3, in which a reduction of about 20% or more in the number of pDCs in the peripheral blood mononuclear cell sample and/or skin biopsy, in response to the administration of DT-IL3, is an indicator for the continuing treatment of the subject.

In certain embodiments, the present disclosure provides DT-IL3 for use in a method of using modulation in the number of pDCs as an indicator for continuing treatment of an autoimmune disease in a subject with DT-IL3 by determining the number of pDCs in a peripheral blood mononuclear cell sample and/or skin biopsy obtained from the subject who has been administered DT-IL3, in which a reduction of about 20% or more reduction in the number of pDCs in the peripheral blood mononuclear cell sample and/or skin biopsy, in response to the administration of DT-IL3, is an indicator for the continuing treatment of the subject.

In certain embodiments, the number of pDCs in the subject is reduced by about 20% to about 95% compared to the subject's sample prior to DT-IL3 administration. For example, the number of pDCs in the subject may be reduced by about 20%, about 30%, about 40%, about 50%, about 60%, about 70%, about 80%, or about 90%. In certain embodiments, the reduction in the number of pDCs in the subject is DT-IL3 dose-dependent.

Methods of measuring numbers of pDCs in a sample (e.g., skin biopsy, peripheral blood mononuclear cell (PBMC)) from a subject are well known in the art and are contemplated herein. For example, in certain embodiments, modulation in pDC numbers is determined by immunohistochemistry or immunofluorescence of a skin lesion biopsy. In certain embodiments, modulation in pDC numbers is determined by flow cytometric based quantification of pDCs in a PBMC sample isolated from the subject. For example, in certain embodiments, quantification of a subject's plasmacytoid dendritic cells (pDCs) in the peripheral blood is performed by flow cytometry. Briefly, mononuclear cells (MNCs) are isolated from the subject's sample by Ficoll Hypaque™ density-gradient centrifugation. After isolation, the MNCs are incubated with a combination of fluorescently labeled antibodies that will specifically bind markers that identify pDCs (e.g., phycoerythrin (PE)-conjugated anti-CD123, anti-HLA-DR Pacific Blue, anti-CD303, anti-CD304 (BDCA-4), anti-BDCA-2, FITC-conjugated lineage [lin] markers including anti-CD3, anti-CD14, anti-CD20). After staining, cells are washed in PBS supplemented with fetal calf serum and then fixed in PBS supplemented with paraformaldehyde. Flow cytometry analysis is then performed: within events corresponding to mononuclear cells by the forward and side scatter profiles, the percentage of $CD123^+$ pDCs is determined within the $HLA-DR^+$, $lin^-$ mononuclear cell population. For example, in certain embodiments, the pDC population is identified as CD14−, CD3−, BDCA4+, CD123+. In certain embodiments, to quantify a subject's pDC numbers, whole blood is collected, and the peripheral blood mononuclear cells are isolated by Ficoll Hypaque™ density-gradient centrifugation. pDCs are then isolated from MNCs by magnetic activated cell sorting using $CD304^+$ magnetic beads (Miltenyi Biotec), enumerated, and the frequency of pDCs is calculated as a percentage of total MNCs.

The number of pDCs can be assessed at one or more points during the period of treatment. For example, in certain embodiments, the number of pDCs in a sample from the treated subject is assessed after the first dose of DT-IL3, and/or after the last dose of DT-IL3, per week of the treatment cycle.

Dosing of DT-IL3

The therapeutic regimens disclosed herein comprise administration of a conjugate of the invention (e.g., DT-IL3) or pharmaceutical compositions thereof to the subject in need thereof. In general, dosages based on body weight are from about 0.01 μg to about 100 mg per kg of body weight, for example, about 0.01 μg to about 10 mg/kg of body weight, about 0.01 μg to about 50 mg/kg of body weight, about 0.01 μg to about 100 mg/kg of body weight, about 0.01 μg to about 10 mg/kg of body weight, about 0.01 μg to about 1 mg/kg of body weight, about 0.01 μg to about 100 μg/kg of body weight, about 0.01 μg to about 20 μg/kg of body weight, about 0.01 g to about 10 μg/kg of body weight, about 0.01 μg to about 1 μg/kg of body weight, about 0.01 g to about 20 μg/kg of body weight, about 0.01 μg to about 10 μg/kg of body weight, about 0.01 μg to about 1.0 μg/kg of body weight, and ranges based on the boundaries of the preceding ranges of concentrations.

The therapeutic regimens disclosed herein comprise administration of a conjugate of the invention (e.g., DT-IL3) or pharmaceutical compositions thereof to the subject in a single dose or in multiple doses (e.g., 2, 3, 4, 5, 6, 7, 8, 10, or more) in the range of about 1 μg/kg to about 100 μg/kg per dose. For example, the DT-IL3 is administered at a dose of 1 μg/kg, 5 μg/kg, 10 μg/kg, 15 μg/kg, 20 μg/kg, 25 μg/kg, 30 μg/kg, 35 μg/kg, 40 μg/kg, 45 μg/kg, 50 μg/kg, 55 μg/kg, 60 μg/kg, 65 μg/kg, 70 μg/kg, 75 μg/kg, 80 μg/kg, 85 μg/kg, 90 μg/kg, 95 μg/kg, or 100 μg/kg. In certain embodiments, the DT-IL3 is administered at a dose in the range of about 5 μg/kg to about 25 μg/kg. For example, the DT-IL3 is administered at a dose of about 5 μg/kg, about 6 μg/kg, about 7 μg/kg, about 8 μg/kg, about 9 μg/kg, about 10 μg/kg, about 11 μg/kg, about 12 μg/kg, about 13 μg/kg, about 14 μg/kg, about 15 μg/kg, about 16 μg/kg, about 17 μg/kg, about 18 μg/kg, about 19 μg/kg, about 20 μg/kg, about 21 μg/kg, about 22 μg/kg, about 23 μg/kg, about 24 μg/kg, or about 25 μg/kg.

In certain embodiments, the methods of treatment provided herein include administration of DT-IL3 or pharmaceutical compositions thereof in single or multiple doses. When administered in multiple doses, the DT-IL3 or pharmaceutical compositions are administered with a frequency and in an amount sufficient to treat and/or manage the autoimmune disease. In certain embodiments, the frequency of administration ranges from once a day up to about once every eight weeks. In certain embodiments, the conjugate is administered once a day. For example, in certain embodiments, the DT-IL3 is administered once daily at a dose in the range of about 5 μg/kg/day to about 25 μg/kg/day. For example, the DT-IL3 is administered at a dose of about 5 μg/kg/day, about 6 μg/kg/day, about 7 μg/kg/day, about 8 μg/kg/day, about 9 μg/kg/day, about 10 μg/kg/day, about 11 μg/kg/day, about 12 μg/kg/day, about 13 μg/kg/day, about 14 μg/kg/day, about 15 μg/kg/day, about 16 μg/kg/day, about 17 μg/kg/day, about 18 μg/kg/day, about 19 μg/kg/day, about 20 μg/kg/day, about 21 μg/kg/day, about 22 μg/kg/day, about 23 μg/kg/day, about 24 μg/kg/day, or about 25 μg/kg/day. In a specific embodiment, the DT-IL3 is administered once daily at a dose of about 5 μg/kg/day. In a specific embodiment, the DT-IL3 is administered once daily at a dose of about 7 μg/kg/day. In a specific embodiment, the DT-IL3 is administered once daily at a dose of about 9 μg/kg/day. In a specific embodiment, the DT-IL3 is administered once daily at a dose of about 12 μg/kg/day. In certain embodiments, the conjugate is administered more than once a day, for example, twice a day, three times a day, four times a day, five or more times a day.

The per day dosages described herein may be administered on consecutive and/or non-consecutive days. In a specific embodiment, a per day dosage is administered on non-consecutive days throughout a week, e.g., Monday, Wednesday, and Friday. In another specific embodiment, a per day dosage is administered on consecutive days throughout a week, e.g. Monday through Sunday.

In certain embodiments, the DT-IL3 is administered once daily for one or more consecutive days. For example, the DT-IL3 is administered once daily for 1 day, 2 days, 3 days, 4 days, 5 days, 6 days, or 7 days. In certain embodiments, the conjugate is administered once a week, twice a week, three times a week, four times a week, five times a week, six times a week, or seven times a week. In certain embodiments, a DT-IL3 is administered at least twice a week (e.g., 2 times, 3 times, 4 times, 5 or more times) in a week or during a treatment cycle.

In certain embodiments, the DT-IL3 is administered in one cycle, for example the treatment cycle is at least one week long (e.g., 1 week, 2 weeks, 3 weeks, 4 weeks, 5 or more weeks). In certain embodiments, the DT-IL3 is administered for multiple cycles, such that each treatment cycle is at least one week long (e.g., 1 week, 2 weeks, 3 weeks, 4 weeks, 5 or more weeks). For example, in an embodiment, the administering of the DT-IL3 is repeated by administering the DT-IL3 for multiple treatment cycles of 2 weeks, 3 weeks, 4 weeks, 5 weeks, 6 weeks, 7 weeks, or 8 or more weeks. In certain embodiments, the administering of the DT-IL3 is repeated by administering the DT-IL3 for at least one dose (e.g., 1 dose, 2 doses, 3 doses, 4 doses, 5 doses, 6 doses, or 7 or more doses) per treatment cycle. In certain embodiments, the administering of the DT-IL3 is repeated by administering the DT-IL3 at 1 to 5 (e.g., 1, 2, 3, 4, 5) doses per treatment cycle. In a certain embodiments, the DT-IL3 is administered once daily for 1-5 consecutive days. For example, in certain embodiments, DT-IL3 is administered once daily for 2 consecutive days in an 8-week treatment cycle at a daily dose of about 5 µg/kg/day to about 25 µg/kg/day. In certain embodiments, DT-IL3 is administered once daily for 3 consecutive days in an 8-week treatment cycle at a daily dose of about 5 µg/kg/day to about 25 µg/kg/day.

The DT-IL3 may be administered repeatedly for an unlimited number of cycles. For example, in certain embodiments, the DT-IL3 is administered for as many cycles as deemed warranted by the attending physician or until disease progression. In certain embodiments, the DT-IL3 is administered for 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50 or more cycles. For example, in certain embodiments, DT-IL3 is administered once daily for 1-5 consecutive days in a 3-8 week treatment cycle at a daily dose of about 5 µg/kg/day to about 25 µg/kg/day, and the treatment cycle is repeated at least once (e.g., 1 time, 2 times, 3 times, 4 times, 5 or more times). For example, in certain embodiments, DT-IL3 is administered once daily for 2 consecutive days in a 3-week treatment cycle at a daily dose of about 5 µg/kg/day to about 25 µg/kg/day, and the treatment cycle is repeated at least once (e.g., 1 time, 2 times, 3 times, 4 times, 5 or more times). In certain embodiments, for example, DT-IL3 is administered once daily for 3 consecutive days in a 3-week treatment cycle at a daily dose of about 5 µg/kg/day to about 25 µg/kg/day, and the treatment cycle is repeated at least once (e.g., 1 time, 2 times, 3 times, 4 times, 5 or more times). For example, in certain embodiments, DT-IL3 is administered once daily for 2 consecutive days in a 4-week treatment cycle at a daily dose of about 5 µg/kg/day to about 25 µg/kg/day, and the treatment cycle is repeated at least once (e.g., 1 time, 2 times, 3 times, 4 times, 5 or more times). In certain embodiments, for example, DT-IL3 is administered once daily for 3 consecutive days in a 4-week treatment cycle at a daily dose of about 5 µg/kg/day to about 25 µg/kg/day, and the treatment cycle is repeated at least once (e.g., 1 time, 2 times, 3 times, 4 times, 5 or more times). For example, in certain embodiments, DT-IL3 is administered once daily for 2 consecutive days in an 8-week treatment cycle at a daily dose of about 5 µg/kg/day to about 25 µg/kg/day, and the treatment cycle is repeated at least once (e.g., 1 time, 2 times, 3 times, 4 times, 5 or more times). In certain embodiments, DT-IL3 is administered, for example, once daily for 3 consecutive days in a 8-week treatment cycle at a daily dose of about 5 µg/kg/day to about 25 µg/kg/day, and the treatment cycle is repeated at least once (e.g., 1 time, 2 times, 3 times, 4 times, 5 or more times).

In certain embodiments, DT-IL3 is administered once daily for 1-3 consecutive days (e.g., 1 day, 2 days, 3 days) in a 3-8 week treatment cycle (e.g., 3 weeks, 4 weeks, 5 weeks, 6 weeks, 7 weeks, 8 weeks) at a daily dose of about 5 µg/kg/day to about 25 µg/kg/day, and the treatment cycle is repeated at least once (e.g., 1 time, 2 times, 3 times, 4 times, 5 or more times). For example, in certain embodiments, DT-IL3 is administered once daily for 1-3 consecutive days (e.g., 1 day, 2 days, 3 days) in a 3-week treatment cycle at a daily dose of about 5 µg/kg/day to about 25 µg/kg/day, and the treatment cycle is repeated at least once (e.g., 1 time, 2 times, 3 times, 4 times, 5 or more times). In certain embodiments, DT-IL3 is administered once daily for 1-3 consecutive days (e.g., 1 day, 2 days, 3 days) in a 4-week treatment cycle at a daily dose of about 5 µg/kg/day to about 25 µg/kg/day, and the treatment cycle is repeated at least once (e.g., 1 time, 2 times, 3 times, 4 times, 5 or more times). In certain embodiments, DT-IL3 is administered once daily for 1-3 consecutive days (e.g., 1 day, 2 days, 3 days) in a 5-week treatment cycle at a daily dose of about 5 µg/kg/day to about 25 µg/kg/day, and the treatment cycle is repeated at least once (e.g., 1 time, 2 times, 3 times, 4 times, 5 or more times). In certain embodiments, DT-IL3 is administered once daily for 1-3 consecutive days (e.g., 1 day, 2 days, 3 days) in a 6-week treatment cycle at a daily dose of about 5 µg/kg/day to about 25 µg/kg/day, and the treatment cycle is repeated at least once (e.g., 1 time, 2 times, 3 times, 4 times, 5 or more times). In certain embodiments, DT-IL3 is administered once daily for 1-3 consecutive days (e.g., 1 day, 2 days, 3 days) in a 7-week treatment cycle at a daily dose of about 5 µg/kg/day to about 25 µg/kg/day, and the treatment cycle is repeated at least once (e.g., 1 time, 2 times, 3 times, 4 times, 5 or more times). In certain embodiments, DT-IL3 is administered once daily for 1-3 consecutive days (e.g., 1 day, 2 days, 3 days) in an 8-week treatment cycle at a daily dose of about 5 µg/kg/day to about 25 µg/kg/day, and the treatment cycle is repeated at least once (e.g., 1 time, 2 times, 3 times, 4 times, 5 or more times).

In certain embodiments, the dosage of a conjugate of the invention is administered as an intravenous infusion over, for example, about 1, 2, 3, 4, 5, 6, 7, 8, 9, 10, 11, 12, 13, 14, 15, 20, 25, 30, 35, 40, 45, 50, 55, 60, 120, 180, or 240 minutes. In certain embodiments, the DT-IL3 is administered as an intravenous infusion over about 15 minutes.

Combination Therapies

The present invention also provides methods for treating, and/or managing an autoimmune disease, involving reducing the number of pDCs in the subject by administering a therapeutically effective amount of a DT-IL3 to the subject and one or more additional therapies, said additional therapy not being a conjugate of the invention. In a specific embodiment, the combination therapies of the invention comprise a pharmaceutical composition in accordance with the invention and at least one other therapy that has the same mechanism of action as said conjugate. In another specific embodiment, the combination therapies of the invention comprise a pharmaceutical composition identified in accordance with the methods of the invention and at least one other therapy (e.g., prophylactic or therapeutic agent), which has a different mechanism of action than said conjugate.

The pharmaceutical composition of the invention and the additional therapy can be administered separately, concurrently, or sequentially. The combination of agents can act additively or synergistically. The combination therapies of the present invention may reduce the side effects associated with the therapies (e.g., prophylactic or therapeutic agents).

The therapeutic agents of the combination therapies can be administered to a subject in the same pharmaceutical composition. Alternatively, the therapeutic agents of the combination therapies can be administered concurrently to a subject in separate pharmaceutical compositions. The prophylactic or therapeutic agents may be administered to a subject by the same or different routes of administration.

Any therapy (e.g., therapeutic or prophylactic agent) which is U.S. Food and Drug Administration (FDA) approved, useful, has been used, or is currently being used for the prevention, treatment, and/or management of an autoimmune disease can be used in compositions and methods of the invention. Such agents include, but are not limited to, Prednisone, Hydroxychloroquine, Chloroquine, Belimumab, Anifrolumab, Abatacept, Atacicept, LUPUZOR™ (rigerimod), Rituximab, Voclosporin, Aldesleukin, Baricitinib, BIIB059, BI655064, Bortezomib, BT063, Cenerimod, Dapirolizumab pegol, Edratide, Filgotinib, GS-9876, Iberdomide, IFN-α kinoid, Iguratimod, Nelfinavir, Obinutuzumab, OMS721, Rapamycin, RC18, RSLV-132, SM101, Theralizumab, Ustekinumab, Vobarilizumab, XmAb5871, Blisibimod, Tabalumab, Epratuzumab, Rigerimod, Tacrolimus, Rontalizumab, Sifalimumab, Anifrolumab, Tocilizumab, Infliximab, Metelimumab, Fresolimumab, Rilonacept, Cyclophosphamide, Methotrexate, Nintedanib, JBT-101, Imatinib, Pirfenidone, Nilotinib, Dasatinib, SAR100842, BMS-986202, BAY41-2272, Riociguat, Resunab, Ixekizumab, Brodalumab, Tralokinumab, Etanercept, Adalimumab, Ustekinumab, Golimumab, Secukinumab, Tildrakizumab, Tofacitinib, and Guselkumab.

In certain embodiments, the combination therapies of the invention comprise a pharmaceutical composition of DT-IL3 in accordance with the invention and at least one agent selected from oligonucleotides, small molecule inhibitors (SMI), antibodies, microRNAs, agomirs, and antagomirs.

Non-limiting examples of oligonucleotides include oligonucleotides that are toll like receptor (TLR) inhibitors, for example, IRS-954, DV-1179, IMO-3100, IMO-8400, IRO-5, and INH-ODN-24888. Non-limiting examples of small molecule inhibitors include inhibitors of a toll like receptor (TLR) pathway such as, HCQ, CpG-52364, SM934, E-6446, AT-791, VTX-763, TMX-302, IMO-9200, ST-2825, AS-2444697, PF-05387252, PF-05388169, PF-06650833, and DZ2002. Exemplary antibodies contemplated by the combination therapies of the present disclosure include, but are not limited to, antibodies that targets a toll like receptor (TLR) or type I IFN pathway such as OPN-305, NI-0101, Mab 9F3, 13H5, ACO-1, AGS-009, Rontalizumab, Sifalimumab, and Anifrolumab.

Protein Conjugate

DT-IL-3 conjugates are known in the art and their administration in accordance with the methods of the present disclosure are contemplated herein. For example, DT-IL-3 conjugates described in U.S. Pat. Nos. 7,763,242; 8,470,307; 9,181,317; and 9,631,006 may be used in accordance with the methods disclosed by the present invention.

A DT-IL3 conjugate of the present disclosure includes the full-length, mature (lacking the signal peptide) interleukin-3 protein (IL-3), or a portion, analog or derivative thereof that binds to the interleukin-3 receptor or a subunit thereof expressed on a cell surface, conjugated through a recombinant technology or through chemical (covalent) bond to diphtheria toxin (DT), or a portion, analog or derivative thereof, which toxin lacks the native cell binding domain. The IL-3 of the present disclosure is human IL-3. In certain embodiments, the conjugate comprises the catalytic and translocation domains of diphtheria toxin fused via a covalent bond to human IL-3. In other embodiments, the diphtheria toxin is linked via a peptide linker to the human IL-3 portion of the conjugate. The linker for the conjugate may be, for example, two, three, four, five, ten, or fifteen amino acids in length. The length of the linker may vary to provide optimal binding of the conjugate. In some embodiments, the peptide linker is two to four amino acids long. The peptide linker may be a His-Met linker. Although not intending to be bound by a particular mechanism of action, the flexible peptide linker facilitates chain pairing and minimizes possible refolding. Linker molecules are commonly known in the art and described in Denardo et al., 1998, *Clin. Cancer Res.* 4:2483-90; Peterson et al., 1999, *Bioconjug. Chem.* 10:553; and Zimmerman et al., 1999, *Nucl. Med. Biol.* 26:943-50 each incorporated by reference in their entireties.

In other embodiments, the invention provides pharmaceutical compositions that include a DT-IL3 of the invention and a pharmaceutically acceptable carrier. In accordance with the present invention, the conjugate can include any domain of DT linked via any linker molecule known in the art to any domain of IL-3. In certain embodiments, the conjugate is DT$_{388}$IL-3, which is a fusion protein of an N-terminal methionine, followed by amino acids 1-388 of DT fused to full-length, mature, human IL-3 via a His-Met amino acid linker.

DT is a protein with three domains: a catalytic domain (amino acids 26-112; bolded sequence within SEQ ID NO: 1 below) connected by an arginine-rich disulfide loop to a translocation domain (amino acids 225-404; italicized sequence within SEQ ID NO: 1 below) followed by a cell binding domain (amino acids 406-559 of SEQ ID NO: 1). Fragments, analogs and derivatives of diphtheria toxin can be useful in the present application. In certain embodiments, the conjugate of the invention consists of the catalytic, the translocation and the cell binding domains of DT. In other embodiments, the conjugate consists of the cell binding and the catalytic domains of DT. In yet other embodiments, the conjugate of the invention consists of the cell binding and the translocation domains of DT. In embodiments, the conjugate of the invention includes the catalytic and translocation domains of DT. In certain embodiments, the conjugate of the invention includes one of either the translocation, catalytic, or cell binding domain.

An exemplary amino acid sequence of DT, accessible from GenBank Accession No. AOU74567.1, is:

```
                                    [SEQ ID NO: 1]
  1 MSRKLFASIL IGALLGIGAP PSAHAGADDV

VDSSKSFVME NFSSYHGTKP GYVDSIQKGI

61 QKPKSGTQGN YDDDWKGFYS TDNKYDAAGY

SVDNENPLSG KAGGVVKVTY PGLTKVLALK

121 VDNAETIKKE LGLSLTEPLM EQVGTEEFIK

RFGDGASRVV LSLPFAEGSS SVEYINNWEQ

181 AKALSVELEI NFETRGKRGQ DAMYEYMAQA

CAGNRVRRSV GSSLSCINLD WDVIRDKTKT

241 KIESLKEHGP IKNKMSESPN KTVSEEKAKQ

YLEEFHQTAL EHPELSELKT VTGINPVFAG

301 ANYAAWAVNV AQVIDSETAD NLEKTTAALS

ILPGIGSVMG IADGAVHHNT EEIVAQSIAL

461 SSLMVAQAIP LVGELVDIGF AAYNFVESII

NLFQVVHNSY NRPAYSPGHK TQPFLHDGYA

421 VSWNTVEDSI IRTGFQGESG HDIKITAENT
```

```
                -continued
        PLPIAGVLLP TIPGKLDVNK SKTHISVNGR

481 KIRMRCRAID GDVTFCRPKS PVYVGNGVHA

NLHVAFHRSS SEKIHSNEIS SDSIGVLGYQ

541 KTVDHTKVNS KLSLFFEIKS
```

Fragments, analogs, and derivatives of IL-3 can be useful in the present invention provided that when fused to the DT portion of the conjugate, such fragments, analogs and derivatives maintain the ability to bind a subunit of the IL-3 receptor or the native IL-3 receptor expressed on the surface of a cell. The binding kinetics of the fragments, analogs or derivatives may remain the same or vary only by not more than 25%. The IL-3 polypeptide may be from any species. In certain embodiments, the IL-3 is a mammalian IL-3, e.g., an IL-3 polypeptide is human IL-3, an analog, derivative, or a fragment thereof. An exemplary amino acid sequence of human IL-3 is:

```
                                    [SEQ ID NO: 2]
      1 MSRLPVLLLL QLLVRPGLQA PMTQTTSLKT

SWVNCSNMID EIITHLKQPP LPLLDFNNLN

61 GEDQDILMEN NLRRPNLEAF NRAVKSLQNA

SAIESILKNL LPCLPLATAA PTRHPIHIKD

121 GDWNEFRRKL TFYLKTLENA QAQQTTLSLA

IF
```

In another embodiment, an IL-3 polypeptide is at least 50%, at least 65%, at least 70%, at least 75%, at least 80%, at least 85%, at least 90%, or at least 95% identical to a native IL-3 amino acid sequence (e.g., a native human IL-3 amino acid sequence).

The DT fragment conjugated to the IL-3 is the catalytic domain and the translocation domain of DT, represented by SEQ ID NO: 3:

```
                                    [SEQ ID NO: 3]
      1 GADDVVDSSK SFVMENFSSY HGTKPGYVDS

IQKGIQKPKS GTQGNYDDDW KGFYSTDNKY

61 DAAGYSVDNE NPLSGKAGGV VKVTYPGLTK

VLALKVDNAE TIKKELGLSL TEPLMEQVGT

121 EEFIKRFGDG ASRVVLSLPF AEGSSSVEYI

NNWEQAKALS VELEINFETR GKRGQDAMYE

181 YMAQACAGNR VRRSVGSSLS CINLDWDVIR

DKTKTKIESL KEHGPIKNKM SESPNKTVSE

241 EKAKQYLEEF HQTALEHPEL SELKTVTGTN

PVFAGANYAA WAVNVAQVID SETADNLEKT

301 TAALSILPGI GSVMGIADGA VHHNTEEIVA

QSIALSSLMV AQAIPLVGEL VDIGFAAYNF

361 VESIINLFQV VHNSYNRPAY SPGHKTRP
```

In some embodiments, the DT fragment is at least 50%, at least 65%, at least 70%, at least 75%, at least 80%, at least 85%, at least 90%, at least 95%, at least 96%, at least 97%, at least 98%, or at least 99% identical to a native DT amino acid sequence.

The conjugates of the present invention can be made by standard recombinant DNA techniques or by protein synthetic techniques, e.g., by use of a peptide synthesizer. For example, a nucleic acid molecule encoding a conjugate of the invention can be synthesized by conventional techniques including automated DNA synthesizers. Alternatively, PCR amplification of gene fragments can be carried out using anchor primers which give rise to complementary overhangs between two consecutive gene fragments which can subsequently be annealed and re-amplified to generate a chimeric gene sequence (see, e.g., *Current Protocols in Molecular Biology*, Ausubel et al., eds., John Wiley & Sons, 1992).

The nucleotide sequences encoding a conjugate of the invention (IL-3 and diphtheria toxin sequences) may be obtained from any information available to those of skill in the art (i.e., from GenBank, the literature, or by routine cloning). The nucleotide sequence coding for a conjugate can be inserted into an appropriate expression vector, i.e., a vector which contains the necessary elements for the transcription and translation of the inserted protein-coding sequence. In some instances, the diphtheria toxin sequence can be truncated in order to remove a specific domain, such as the targeting domain. The techniques for modifying or truncating DNA are well known to those of skill in the art of molecular biology. Also, the IL-3 and the diphtheria toxin sequences can be ligated in such a way as to generate a DNA sequence that, when translating, creates a polypeptide that is a compound of the invention. In certain embodiments, a linker sequence is introduced into the recombinant sequence that links the IL-3 sequence and the diphtheria toxin sequence. A variety of host-vector systems may be utilized in the present invention to express the protein-coding sequence. These include but are not limited to mammalian cell systems infected with virus (e.g., vaccinia virus, adenovirus, etc.); insect cell systems infected with virus (e.g., baculovirus); microorganisms such as yeast (e.g. *Pichia*) containing yeast vectors; or bacteria (for example, *E. coli*) transformed with bacteriophage, DNA, plasmid DNA, or cosmid DNA. The expression elements of vectors vary in their strengths and specificities. Depending on the host-vector system utilized, any one of a number of suitable transcription and translation elements may be used. In a specific embodiment, the protein is expressed in *E. coli*. In another specific embodiment, the protein is expressed in *Pichia*.

The expression of a conjugate of the invention may be controlled by any promoter or enhancer element known in the art. In a specific embodiment, the expression of a conjugate of the invention is regulated by a constitutive promoter. In another embodiment, the expression is regulated by an inducible promoter. In another embodiment, the expression is regulated by a tissue-specific promoter.

In a specific embodiment, a vector is used that comprises a promoter operably linked to a conjugate-encoding nucleic acid, one or more origins of replication and, optionally, one or more selectable markers (e.g., an antibiotic resistance gene).

Expression vectors containing inserts of a gene encoding a conjugate can be identified by three general approaches: (a) nucleic acid hybridization, (b) presence or absence of "marker" gene functions, and (c) expression of inserted sequences. In the first approach, the presence of a gene encoding a conjugate in an expression vector can be detected by nucleic acid hybridization using probes, which include sequences that are homologous to an inserted gene encoding the conjugate. In the second approach, the recombinant vector/host system can be identified and selected based upon the presence or absence of certain "marker" gene functions (e.g., thymidine kinase activity, resistance to antibiotics, transformation phenotype, occlusion body formation in baculovirus, etc.) caused by the insertion of a nucleotide sequence encoding a conjugate in the vector. For example, if the nucleotide sequence encoding the conjugate is inserted within the marker gene sequence of the vector, recombinants containing the gene encoding the conjugate insert can be identified by the absence of the marker gene function. In the third approach, recombinant expression vectors can be identified by assaying the gene product (e.g., conjugate) expressed by the recombinant. Such assays can be based, for example, on the physical or functional properties of the conjugate in in vitro assay systems, e.g., binding to an antibody or the IL-3 receptor.

For long-term, high-yield production of recombinant conjugates, stable expression is preferred. For example, cell lines which stably express the conjugate of the invention may be engineered. Rather than using expression vectors which contain viral origins of replication, host cells can be transformed with DNA controlled by appropriate expression control elements (e.g., promoter, enhancer, sequences, transcription terminators, polyadenylation sites, etc.), and a selectable marker. Following the introduction of the foreign DNA, engineered cells may be allowed to grow for 1-2 days in an enriched medium, and then are switched to a selective medium. The selectable marker in the recombinant plasmid confers resistance to the selection and allows cells to stably integrate the plasmid into their chromosomes and grow to form foci which in turn can be cloned and expanded into cell lines. This method may advantageously be used to engineer cell lines which express a conjugate of the invention.

The DT-IL3 of the present disclosure is generally produced recombinantly, using bacterial, insect, or mammalian cells containing a nucleic acid engineered to express the conjugate protein, as described above.

Once a conjugate of the invention has been produced by recombinant expression or by chemical synthesis, it may be purified by any method known in the art for purification of a protein, for example, by chromatography (e.g., ion exchange, affinity, particularly by affinity for the specific antigen after Protein A, and sizing column chromatography), centrifugation, differential solubility, or by any other standard technique for the purification of proteins.

Pharmaceutical Compositions

The present invention provides compositions that include DT-IL3 for use in accordance with the methods of the present disclosure. In particular, the invention provides a pharmaceutical composition, which include an effective amount/dose of DT-IL3 and a pharmaceutically acceptable carrier or vehicle. In a specific embodiment, a pharmaceutical composition includes an effective amount/dose of DT-IL3 and a pharmaceutically acceptable carrier or vehicle. The pharmaceutical compositions are suitable for veterinary and/or human administration. The pharmaceutical compositions are also suitable for treatment of an autoimmune disease (e.g., SSc) in a subject.

The compositions can be in the form of a solid or liquid. Typical routes of administration may include parenteral. Parenteral administration includes subcutaneous injections, intravenous, intramuscular, intraperitoneal, intrapleural, intrasternal injection or infusion techniques. In a specific embodiment, the compositions are administered parenterally. In a more specific embodiment, the compositions are administered intravenously. Pharmaceutical compositions can be formulated so as to allow DT-IL3 to be bioavailable upon administration of the composition to a subject. Compositions can take the form of one or more dosage units.

EXAMPLES

In order that the invention described herein can be more fully understood, the following examples are set forth. It should be understood that these examples are included merely for purposes of illustration of certain aspects and embodiments of the present invention, and are not to be construed as limiting the invention in any manner. Reasonable variations, such as those that occur to a reasonable artisan, can be made herein without departing from the scope of the present invention.

Example 1—DT-IL3 Selectively Kills pDCs from Healthy Volunteers and Systemic Sclerosis (SSc) Patients In this example, in an ex vivo experiment, the ability of DT-IL3 to specifically target and mediate killing of pDCs from healthy volunteers and SSc patients was evaluated. SSc patients used in this study fulfilled the 2013 American College of Rheumatology/European League Against Rheumatism (ACR/EULAR) classification criteria for SSc.

PBMCs from fresh blood were prepared using Ficoll-Paque® density gradient. Due to the low frequency of pDCs in peripheral blood, pDCs were isolated using anti-BDCA4 magnetic beads from one PBMC fraction and added to the remaining PBMC fraction. pDC-enriched PBMCs (3-6% pDCs) were cultured at $2 \times 10^5$ cells per well and incubated with DT-IL3 at various concentrations (0.01-100 ng/ml) in the presence or absence of the TLR9 ligand CpG-274 (0.5 mM) at 37° C., 5% $CO_2$, and 95% humidity. TLR9 activation by CpG-274 was used to mimic the chronic activation of pDCs that characterizes autoimmune diseases. After 24 or 48 hours of culture, pDC survival was assessed by flow cytometry using antibodies directed to CD14, CD3, BDCA4, and CD123. The pDC population was identified as CD14−, CD3−, BDCA4+, CD123+. To evaluate the effects of DT-IL3 on the survival of B cells and T cells, after the pDC-enriched PBMCs were cultured for 24 or 48 hours at various concentrations of DT-IL3 (0.001-1000 ng/ml), flow cytometry was performed using antibodies directed to CD3, CD4, CD8, and CD20. T cells were identified as CD3+ CD4+ or CD3+ CD8+, and B cells were identified as CD20+.

Figure 1B:
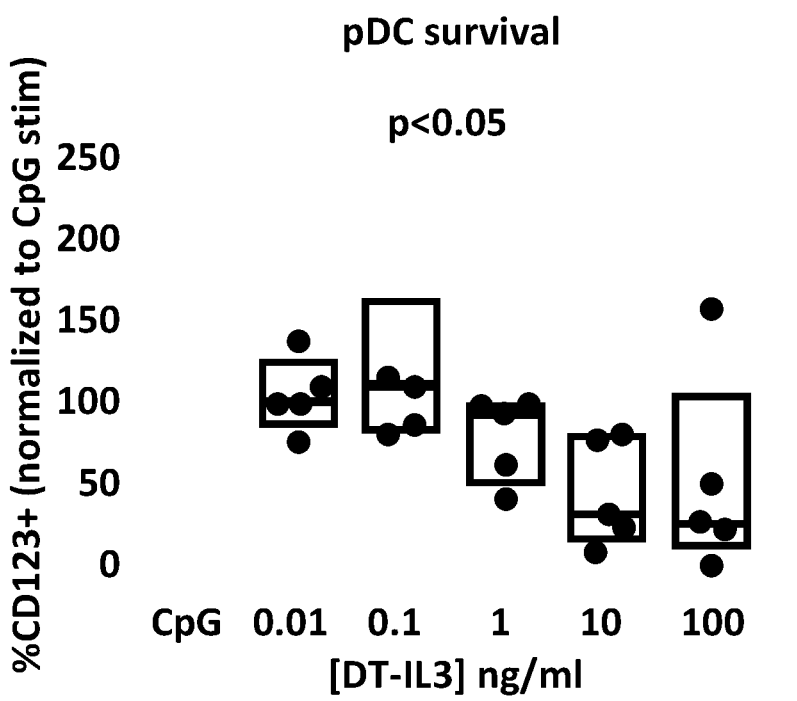
Figure 1C:
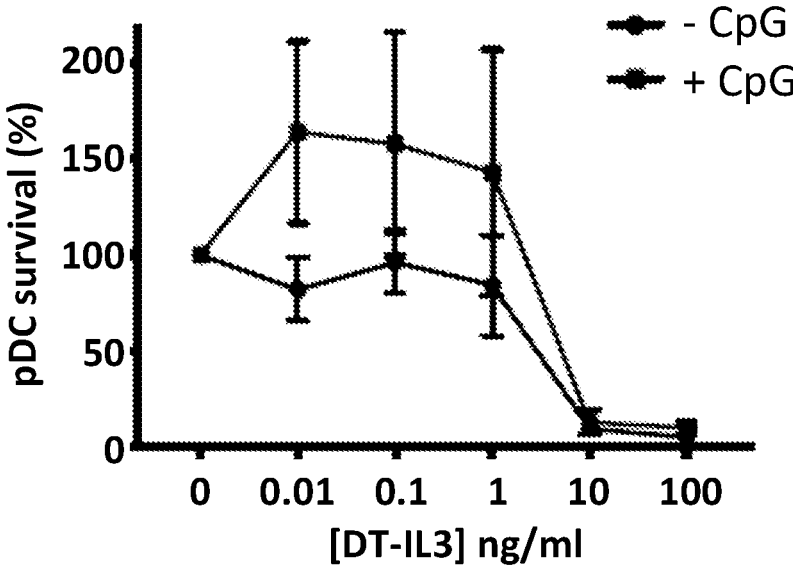
Figure 1D:
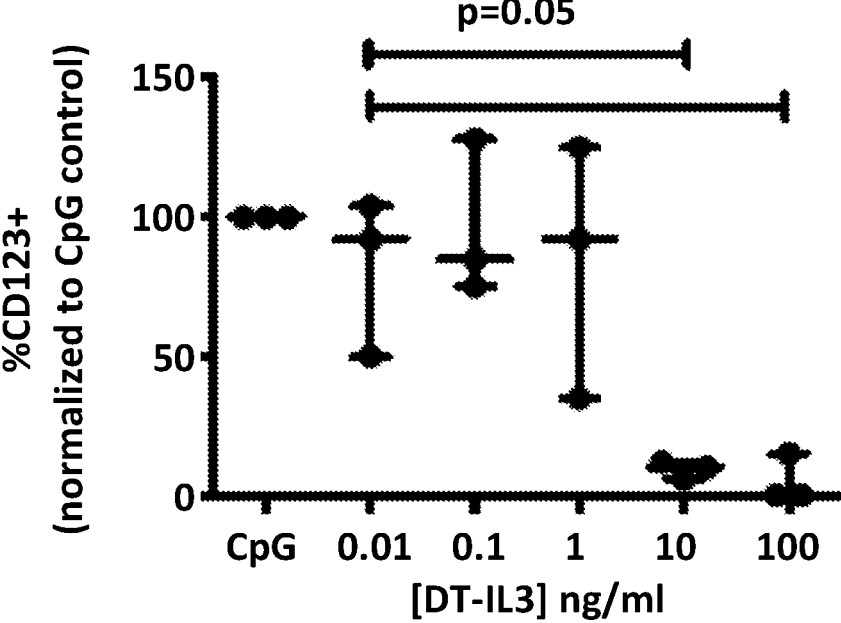
Figure 1E:
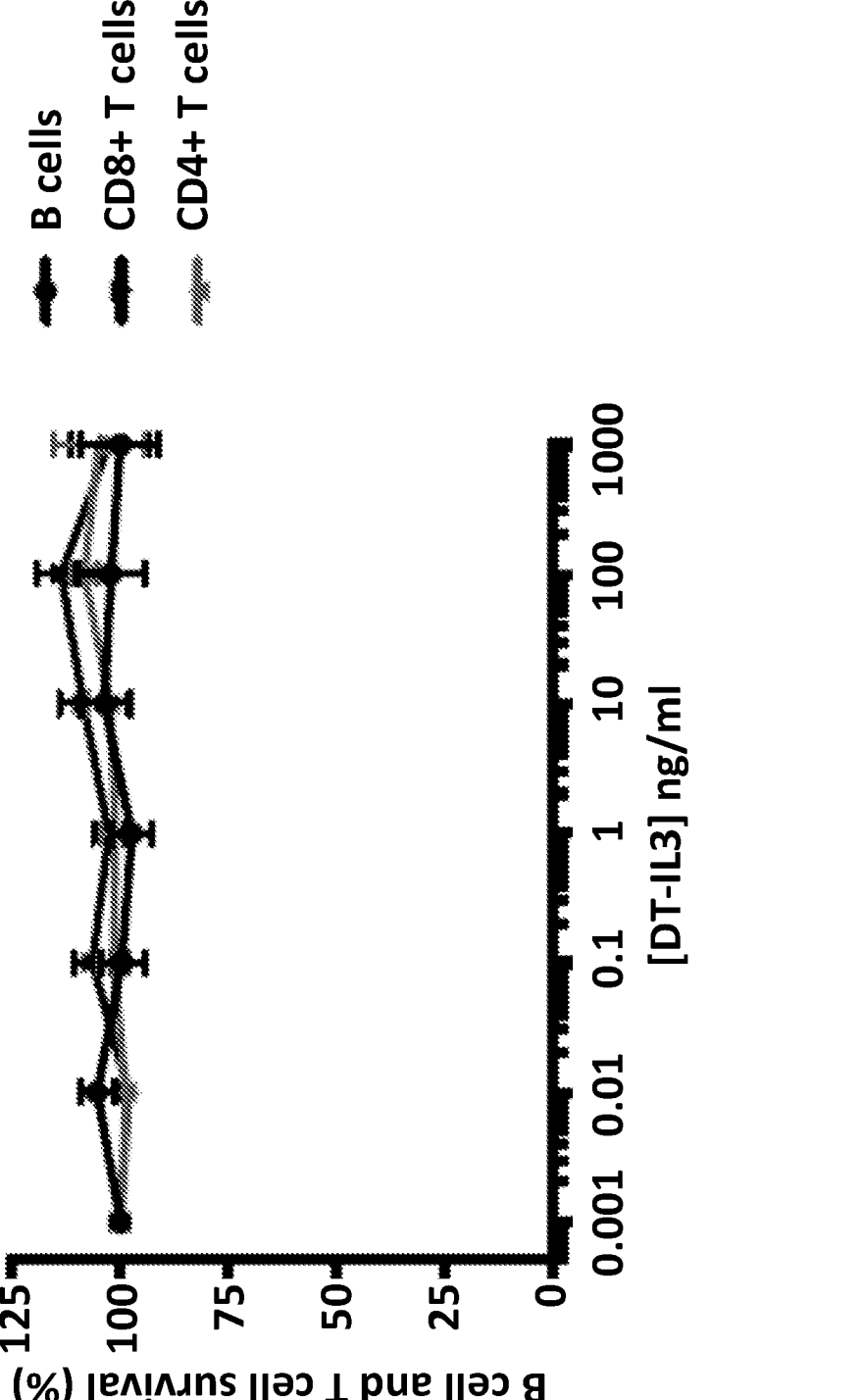

As shown in FIGS. 1A-1E, DT-IL3 was cytotoxic towards pDCs obtained from healthy volunteers (FIGS. 1A-1B) and SSc patients (FIGS. 1C-1D) but no effect was observed on B cells or T cells across the tested range of DT-IL3 concentrations in healthy volunteers (FIG. 1E). Altogether, these data indicate that DT-TL3 selectively targets and eliminates pDCs from PBMCs of healthy volunteers and SSc patients.

Example 2—an In Vitro Model for DT-IL3 Mediated Targeting of Activated pDCs

Figure 2:
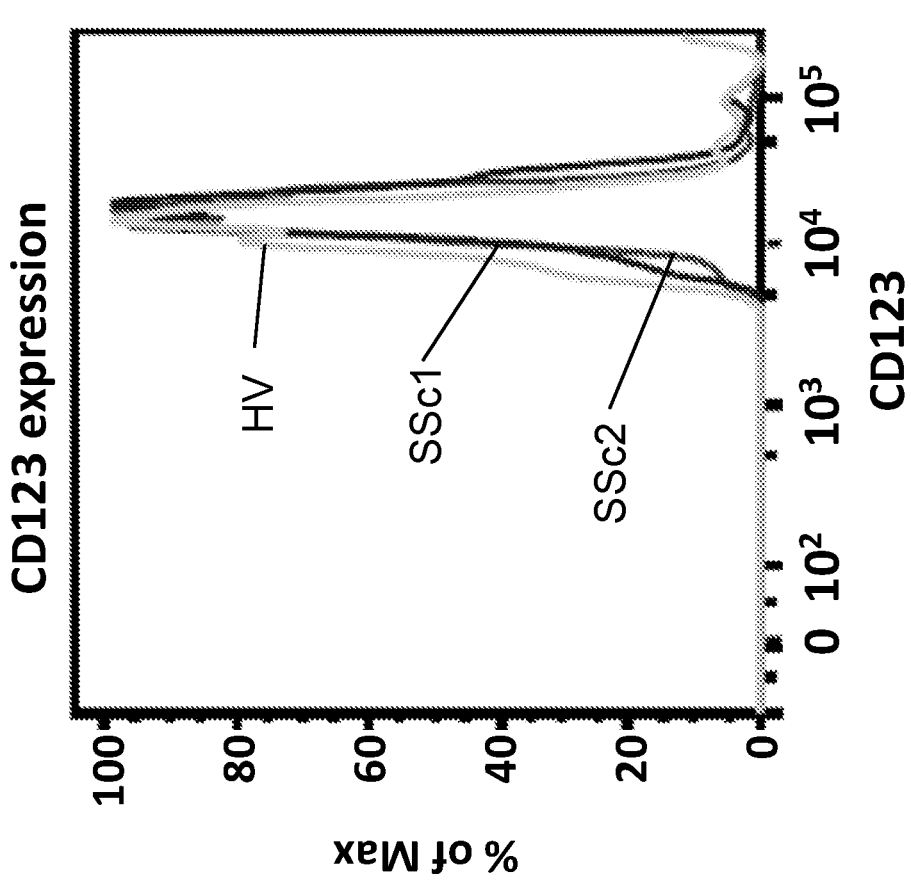
FIG. 2 is an image of flow cytometry data showing the expression of CD123 (IL-3R□) in pDCs from healthy volunteers (HV) and SSc patients (SSc1 and SSc2).

In this example, an in vitro system for modeling the effects and targeting of chronically activated pDCs was evaluated. The comparable levels of expression in CD123 (IL-3Rα) observed in pDCs from healthy volunteer (HV) and SSc donors (FIG. 2) suggested that targeting of pDCs in SSc could be modeled with results obtained from healthy volunteers.

PBMCs from fresh blood samples of healthy volunteers were isolated and treated with DT-IL3 in the presence or absence of CpG-274 as described in Example 1.

Figure 3A:
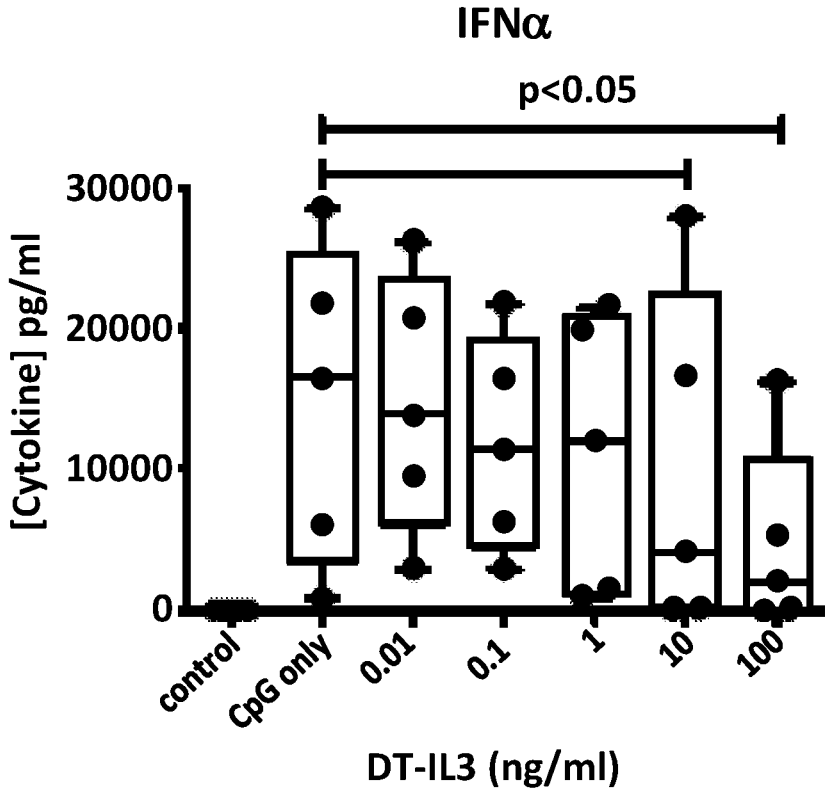
FIGS. 3A-D provide a series of graphs quantifying the secretion of IFN-α (FIGS. 3A-3B) and IL-6 (FIGS. 3C-3D) by CpG-274-stimulated PBMCs from healthy volunteers treated with increasing doses of DT-IL3.
Figure 3B:
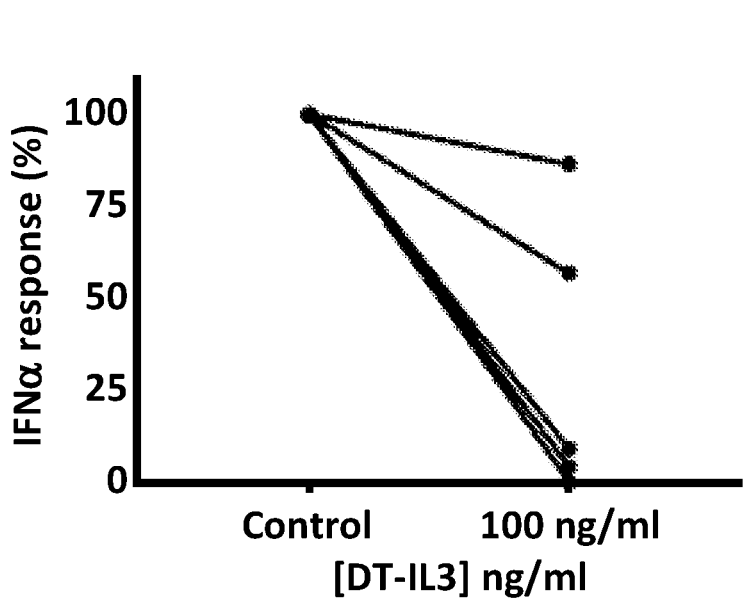
Figure 3C:
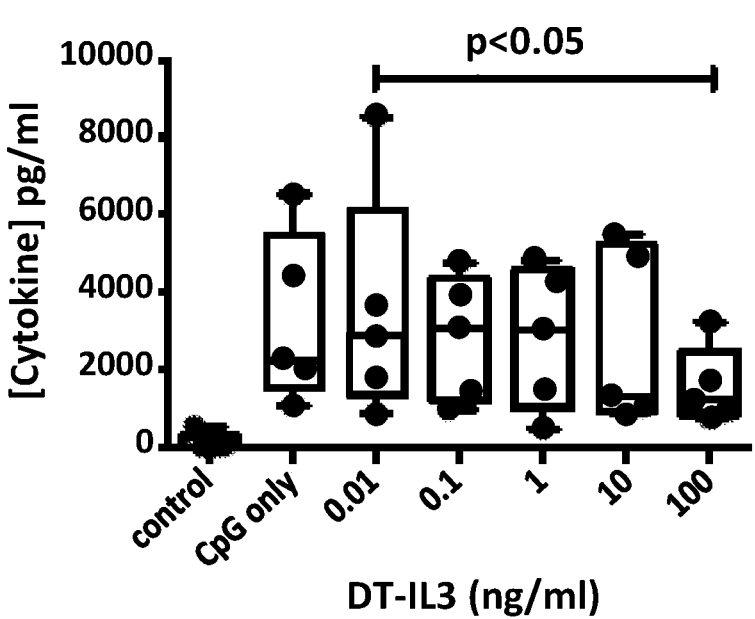
Figure 3D:
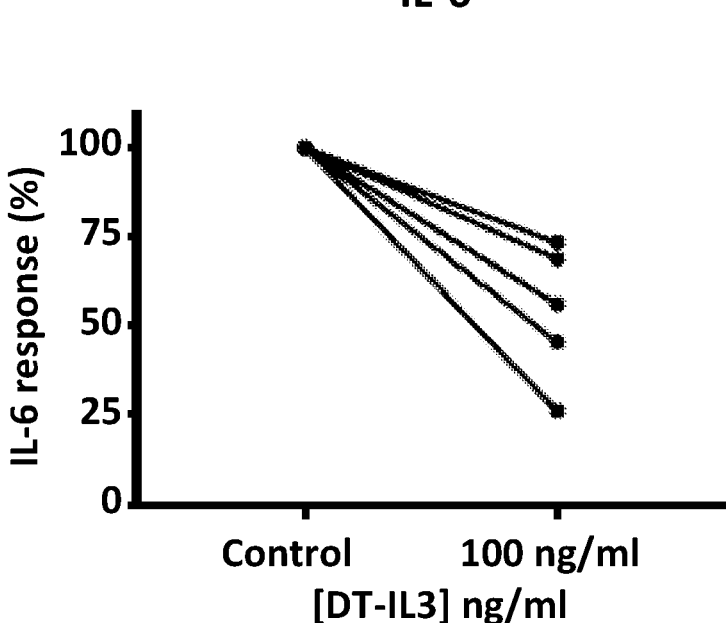

As shown in FIGS. 1A-1B, DT-IL3 was significantly cytotoxic to TLR9 activated pDCs from healthy volunteers. Furthermore, DT-IL3 mediated pDC depletion was accompanied by significant reductions in CpG-induced secretion of IFNα (FIGS. 3A-3B) and IL-6 (FIGS. 3C-3D).

PBMCs from SSc patients were also isolated and treated with DT-IL3 in the presence or absence of CpG-274 as described in Example 1. As shown in FIGS. 1C-1D, DT-IL3 was significantly cytotoxic to TLR9 activated pDCs.

These data demonstrate that DT-IL3 mediated killing of the activated pDCs significantly reduces pro-inflammatory cytokine secretion.

Example 3—Treatment of SSc with DT-IL3

Patients in this study fulfill the 2013 ACR/EULAR classification criteria for SSc and have a minimum skin score of 15. Exclusion criteria include renal involvement and severe interstitial lung disease.

A cohort of 10-15 SSc patients with varying degrees of disease progression (early and late stage SSc) are intravenously administered DT-IL3 (infusion over 15 minutes) once daily at a dose of 7 µg/kg/day for 1-5 consecutive days (e.g., 1 day, 2 days, or 3 days) in a 3-8 week treatment cycle (e.g., 3 weeks, 4 weeks, 5 weeks, 6 weeks, 7 weeks, or 8 weeks). After 3-8 weeks of the first administration of DT-IL3 on day 1, the patients undergo another 3-8 week cycle of intravenous DT-IL3 administration, as described above. Administration of DT-IL3 is repeated for multiple cycles (e.g., 2 cycles, 3 cycles, 4 cycles, or 5 cycles).

In another treatment regimen, a cohort of SSc patients with varying degrees of disease progression (early and late stage SSc) are intravenously administered DT-IL3 (infusion over 15 minutes) once daily at a dose of 7 µg/kg/day for 1-5 days (e.g., 1 day, 2 days, or 3 days) in a 3-8 week treatment cycle. If none of the patients in the 7 µg/kg/day cohort experience a dose-limiting toxicity, another SSc patient cohort is treated at the higher dose of 9 µg/kg/day DT-IL3 for 1-5 days (e.g., 1 day, 2 days, or 3 days) in a 3-8 week treatment cycle. However, if some patients from the 7 µg/kg/day cohort experience a dose-limiting toxicity, more patients are treated at the same dose level. The cycle of dose escalation is continued (e.g., 12 µg/kg/day, 16 µg/kg/day) until at least 33% of patients experience a dose-limiting toxicity at the current dose level.

Patients are monitored for toxicities using the NCI Common Terminology Criteria for Adverse Events (CTCAE). Vital signs are measured frequently on the days of treatment. Careful input/output is recorded daily. CBC, CMP, coagulation panel, LDH, uric acid, and magnesium are tested daily. Blood is drawn for clinical pharmacology studies including pharmacokinetics and immune response.

The effect of DT-IL3 treatment on disease symptoms and/or disease burden is monitored using the mRSS. Additionally, skin thickness, collagen content, levels of α-smooth muscle actin positive cells, and levels of fibroblast activation are observed from patient biopsies. It is contemplated that administration of DT-IL3 will reduce SSc symptoms, will improve the mRSS scores, and be effective at treating SSc.

Example 4—Monitoring SSc Patients Treated with DT-IL3

Patients in this study fulfill the 2013 ACR/EULAR classification criteria for SSc and have a minimum skin score of 15. Exclusion criteria include renal involvement and severe interstitial lung disease.

Prior to commencing treatment, peripheral blood mononuclear cell samples or skin biopsies are isolated from a cohort of SSc patients with varying degrees of disease progression (early and late stage SSc). The number of pDCs and the levels of one or more cytokines and/or chemokines (e.g., CXCL4, CXCL9, CXCL10, IFN-α, IL-6, IP-10, TNF-α, IFN-γ, IL-8, Rantes, MIP1α, MIP1β, or MCP1) in the samples are then determined. The patients are then intravenously administered DT-IL3 (infusion over 15 minutes) once daily at a dose of 7 µg/kg/day for 1-5 consecutive days (e.g., 2 days or 3 days) in a 3-8 week treatment cycle (e.g., 3 weeks, 4 weeks, 5 weeks, 6 weeks, 7 weeks, or 8 weeks). After the first and/or last dose of DT-IL3 for each week in the first cycle, pDC numbers and levels of one or more cytokines and/or chemokines are again measured in peripheral blood mononuclear cell samples or skin biopsies from the patients. Subsequently, the patients undergo multiple alternating phases of 3-8 week cycles of intravenous DT-IL3 administration, and pDC numbers and cytokine and/or chemokine expression levels in patient samples are measured. Administration of DT-IL3 is repeated for multiple cycles (e.g., 2 cycles, 3 cycles, 4 cycles, or 5 cycles).

It is contemplated that treatment with DT-IL3 will cause varied degrees of reduction in pDCs (e.g., about 20% to about 95%). The number of pDCs in a peripheral blood sample and/or skin biopsy is used as an indicator for the continuing treatment of the patient or to inform clinical dosing regimen and related clinical decisions.

It is also contemplated that treatment with DT-IL3 will cause reductions in the levels of the measured cytokine and/or chemokine. Thus, the levels of the measured cytokine and/or chemokine are used to monitor the effectiveness of DT-IL3 therapy.

In another treatment cohort, peripheral blood mononuclear cell samples or skin biopsies are isolated from a cohort of SSc patients with varying degrees of disease progression (early and late stage SSc). Levels of one or more type I IFN-inducible genes (e.g., IFI27, IFI30, IFI6, IRF1, IFITM1, IFITM2, IFIT1, CXCL9, CXCL10, RSAD2, IFI44, IFI44L, IFI6, GBP1, MxB, SERPING1, LY6E, XAF3, IFIT2, IFIT3, MxA, or IRF7) in the samples are then determined. The patients are then intravenously administered DT-IL3 (infusion over 15 minutes) once daily at a dose of 7 µg/kg/day for 1-5 consecutive days (e.g., 1 day, 2 days, or 3 days) in a 3-8 week treatment cycle (e.g., 3 weeks, 4 weeks, 5 weeks, 6 weeks, 7 weeks, or 8 weeks). After the first and/or last dose of DT-IL3 for each week in the first cycle, levels of one or more type I IFN-inducible genes are again measured in PBMC samples or skin biopsies from the patients. Subsequently, the patients undergo multiple alternating phases of 3-8 week cycles of intravenous DT-TL3 administration and measurement of type I IFN-inducible gene expression levels. Administration of DT-IL3 is repeated for multiple cycles (e.g., 2 cycles, 3 cycles, 4 cycles, or 5 cycles).

It is contemplated that treatment with DT-IL3 will cause reductions in the levels of the measured type I IFN-inducible gene. Thus, the levels of the measured type I IFN-inducible gene are used to monitor the effectiveness of DT-IL3 therapy.

Example 5: Embodiments

The following numbered items represent certain embodiments.

Embodiment 1. A method of treating an autoimmune disease in a human subject, the method comprising reducing the number of plasmacytoid dendritic cells (pDCs) in the subject by administering a therapeutically effective dose of a human interleukin-3 (IL-3)-diphtheria toxin conjugate (DT-TL3) to the subject.

Embodiment 2. A human interleukin-3 (IL-3)-diphtheria toxin conjugate (DT-IL3) for use in a method of treating an autoimmune disease in a human subject, the method comprising: reducing the number of plasmacytoid dendritic cells (pDCs) in the subject by administering a therapeutically effective dose of DT-IL3 to the subject.

Embodiment 3. The method of embodiment 1 or the DT-TL3 for the use according to embodiment 2, wherein the reduction in the number of pDCs is accomplished through selective killing of pDCs by the administered DT-TL3.

Embodiment 4. The method of embodiment 1 or 3, or the DT-TL3 for the use according to embodiment 2 or 3, wherein the autoimmune disease is selected from lupus (e.g., systemic lupus erythematosus, cutaneous lupus, discoid lupus), Sjogren's syndrome, inflammatory arthritis, systemic sclerosis (SSc), morphea, psoriasis, lichen planus, dermatomyositis, lichen sclerosus, and cutaneous graft-versus-host disease (GVHD), adrenergic drug resistance, alopecia areata, ankylosing spondylitis, antiphospholipid syndrome, autoimmune Addison's disease, autoimmune diseases of the adrenal gland, allergic encephalomyelitis, autoimmune hemolytic anemia, autoimmune hepatitis, autoimmune inflammatory eye disease, autoimmune neonatal thrombocytopenia, autoimmune neutropenia, autoimmune oophoritis and orchitis, autoimmune thrombocytopenia, autoimmune thyroiditis, Behcet's disease, bullous pemphigoid, cardiomyopathy, cardiotomy syndrome, celiac sprue-dermatitis, chronic active hepatitis, chronic fatigue immune dysfunction syndrome (CFIDS), chronic inflammatory demyelinating polyneuropathy, Churg-Strauss syndrome, cicatricial pemphigoid, CREST syndrome, cold agglutinin disease, Crohn's disease, dense deposit disease, essential mixed cryoglobulinemia, fibromyalgia-fibromyositis, glomerulonephritis (e.g., IgA nephropathy), gluten-sensitive enteropathy, Goodpasture's syndrome, Graves' disease, Guillain-Barre, hyperthyroidism (i.e., Hashimoto's thyroiditis), idiopathic pulmonary fibrosis, idiopathic Addison's disease, idiopathic thrombocytopenia purpura (ITP), IgA neuropathy, juvenile arthritis, Meniere's disease, mixed connective tissue disease, multiple sclerosis, Myasthenia Gravis, myocarditis, type 1 or immune-mediated diabetes mellitus, neuritis, other endocrine gland failure, pemphigus vulgaris, pernicious anemia, polyarteritis *nodosa*, polychondritis, polyendocrinopathies, polyglandular syndromes, polymyalgia rheumatica, polymyositis, post-MI, primary agammaglobulinemia, primary biliary cirrhosis, psoriatic arthritis, Raynaud's phenomenon, relapsing polychondritis, Reiter's syndrome, rheumatic heart disease, rheumatoid arthritis, sarcoidosis, stiff-man syndrome, takayasu arteritis, temporal arteritis/giant cell arteritis, ulcerative colitis, urticaria, uveitis, Uveitis Ophthalmia, vasculitides such as dermatitis herpetiformis vasculitis, vitiligo, and Wegener's granulomatosis.

Embodiment 5. The method of embodiment 4, or the DT-IL3 for the use according to embodiment 4, wherein the autoimmune disease is lichen planus, dermatomyositis, lichen sclerosus, or cutaneous graft-versus-host disease (GVHD).

Embodiment 6. The method of embodiment 4, or the DT-IL3 for the use according to embodiment 4, wherein the autoimmune disease is morphea or SSc.

Embodiment 7. The method of embodiment 6, or the DT-IL3 for the use according to embodiment 6, wherein the SSc is limited SSc, diffuse SSc, early-onset SSc, or late-onset SSc.

Embodiment 8. The method of embodiment 4, or the DT-IL3 for the use according to embodiment 4, wherein the autoimmune disease is psoriasis.

Embodiment 9. The method of embodiment 4, or the DT-IL3 for the use according to embodiment 4, wherein the autoimmune disease is systemic lupus erythematosus or cutaneous lupus.

Embodiment 10. The method of any one of embodiments 4-9, or the DT-IL3 for the use according to any one of embodiments 4-9, wherein the subject has been determined to have elevated expression of at least one type I IFN-inducible gene.

Embodiment 11. The method of embodiment 10, or the DT-IL3 for the use according to embodiment 10, wherein the type I IFN-inducible gene is selected from IFI27, IFI30, IFI6, IRF1, IFITM1, IFITM2, IFIT1, CXCL9, CXCL10, RSAD2, IFI44, IFI44L, IFI6, GBP1, MxB, SERPING1, LY6E, XAF3, IFIT2, IFIT3, MxA, and IRF7.

Embodiment 12. The method of any one of embodiments 4-9, or the DT-TL3 for the use according to any one of embodiments 4-9, wherein the subject exhibits presence of a type I IFN-inducible gene signature in the skin.

Embodiment 13. The method of embodiment 12, or the DT-IL3 for the use according to embodiment 12, wherein the type I IFN-inducible gene signature comprises an increased expression compared to healthy individuals of at least one gene selected from IFI27, IFI30, IFI6, IRF1, IFITM1, IFITM2, IFIT1, CXCL9, CXCL10, RSAD2, IFI44, IFI44L, IFI6, GBP1, MxB, SERPING1, LY6E, XAF3, IFIT2, IFIT3, MxA, and IRF7.

Embodiment 14. The method of any one of embodiments 4-9, or the DT-TL3 for the use according to any one of embodiments 4-9, wherein the subject exhibits elevated levels of type I interferons or IFN-α compared to healthy individuals.

Embodiment 15. The method of any one of embodiments 1 or 3-14, or the DT-IL3 for the use according to any one of embodiments 2-14, wherein the reduction in the number of pDCs results in reduced levels of at least one type I IFN-inducible gene or reduced levels of at least one type I interferon.

Embodiment 16. The method of embodiment 7, or the DT-IL3 for the use according to embodiment 7, wherein the reduction in the number of pDCs results in an amelioration of SSc symptoms or a reduction in SSc characterized by at least one of: reduced skin thickness, reduced collagen content, reduced levels of α-smooth muscle actin positive cells, reduced levels of fibroblast activation, reduced levels of IFN-inducible genes, or improvement of the subject's Modified Rodnan Skin Score (mRSS) score.

Embodiment 17. The method of any one of embodiments 1 or 3-16, or the DT-IL3 for use according to any one of embodiments 2-16, wherein the therapeutically effective dose of DT-TL3 is in the range of 1 μg/kg to 100 μg/kg.

Embodiment 18. The method of embodiment 17, or the DT-IL3 for use according to embodiment 17, wherein the therapeutically effective dose of DT-IL3 is administered once daily at a dose in the range of 5 μg/kg to 25 μg/kg.

Embodiment 19. The method of embodiment 18, or the DT-IL3 for use according to embodiment 17, wherein the therapeutically effective dose of DT-IL3 is administered once daily at a dose of 7 μg/kg, 9 μg/kg, 12 μg/kg, or 16 μg/kg.

Embodiment 20. The method of any one of embodiments 17 to 19, or the DT-IL3 for use according to any one of embodiments 17 to 19, wherein the administering of the therapeutically effective dose of DT-IL3 is repeated by administering the DT-TL3 for treatment cycles of 1 week, 2 weeks, 3 weeks, 4 weeks, 5 weeks, 6 weeks, 7 weeks, or 8 or more weeks.

Embodiment 21. The method of embodiment 20, or the DT-IL3 for use according to embodiment 20, wherein the administering of the therapeutically effective dose of DT-IL3 is repeated by administering the DT-IL3 at 1, 2, 3, 4, or 5 times per treatment cycle.

Embodiment 22. The method of embodiment 21, or the DT-IL3 for use according to embodiment 21, wherein the administering of the therapeutically effective dose of DT-IL3 is once daily for 1, 2, 3, 4, or 5 consecutive days per treatment cycle.

Embodiment 23. The method of any one of embodiments 17-22, or the DT-IL3 for use according to any one of embodiments 17-22, wherein the administration of the therapeutically effective dose of DT-IL3 does not affect the number of T cells or B cells in the subject.

Embodiment 24. A method of using modulation in the levels of a cytokine or chemokine to monitor the effectiveness of a therapeutic treatment of an autoimmune disease in a subject, the method comprising: a) administering a human interleukin-3 (IL-3)-diphtheria toxin conjugate (DT-IL3) to the subject; and b) subsequently determining levels of at least one cytokine or chemokine in a sample obtained from the subject.

Embodiment 25. A human interleukin-3 (IL-3)-diphtheria toxin conjugate (DT-IL3) for use in a method of using modulation in the levels of a cytokine or chemokine to monitor the effectiveness of a therapeutic treatment of an autoimmune disease in a subject, the method comprising: a) administering the DT-IL3 to the subject; and b) subsequently determining levels of at least one cytokine or chemokine in a sample obtained from the subject.

Embodiment 26. The method of embodiment 24, or the DT-IL3 for use according to embodiment 23, wherein the sample is a peripheral blood mononuclear cell sample or a skin biopsy.

Embodiment 27. The method of embodiment 24 or 26, or the DT-TL3 for the use according to embodiment 23 or 24, wherein the at least one cytokine or chemokine is selected from CXCL4, CXCL9, CXCL10, IFN-α, IL-6, TNF-α, IFN-γ, IL-8, Rantes, MIP1α, MIP1(3, and MCP1.

Embodiment 28. The method of embodiment 27, or the DT-IL3 for the use according to embodiment 25, wherein subsequent to the administration of DT-IL3, levels of the at least one cytokine or chemokine is determined to be reduced.

Embodiment 29. A method of using modulation in the levels of a type I IFN-inducible gene to monitor the effectiveness of a therapeutic treatment of an autoimmune disease in a subject, the method comprising: a) administering a human interleukin-3 (IL-3)-diphtheria toxin conjugate (DT-TL3) to the subject; and b) subsequently determining expression levels of at least one type I IFN-inducible gene in a sample obtained from the subject.

Embodiment 30. A human interleukin-3 (IL-3)-diphtheria toxin conjugate (DT-IL3) for use in a method of using modulation in the levels of a type I IFN-inducible gene to monitor the effectiveness of a therapeutic treatment of an autoimmune disease in a subject, the method comprising: a) administering the DT-TL3 to the subject; and b) subsequently determining expression levels of at least one type I IFN-inducible gene in a sample obtained from the subject.

Embodiment 31. The method of embodiment 27, or the DT-IL3 for use according to embodiment 28, wherein the sample is a peripheral blood mononuclear cell sample or a skin biopsy.

Embodiment 32. The method of embodiment 29 or 31, or the DT-IL3 for the use according to embodiment 29 or 31, wherein the at least one type I IFN-inducible gene is selected from IFI27, IFI30, IFI6, IRF1, IFITM1, IFITM2, IFIT1, CXCL9, CXCL10, RSAD2, IFI44, IFI44L, IFI6, GBP1, MxB, SERPING1, LY6E, XAF3, IFIT2, IFIT3, MxA, and IRF7.

Embodiment 33. The method of embodiment 32, or the DT-IL3 for the use according to embodiment 30, wherein subsequent to the administration of DT-IL3, levels of the at least one type I IFN-inducible gene is determined to be reduced.

Embodiment 34. The method of any one of embodiments 1, 3-24, 26-29, or 31-33, or the DT-IL3 for the use according to any one of embodiments 2-23, 25-28, or 30-33, wherein the DT-IL3 is formulated for intravenous (IV) administration.

Embodiment 35. The method of any one of embodiments 1, 3-24, 26-29, or 31-34, or the DT-IL3 for the use according to any one of embodiments 2-23, 25-28, or 30-34, wherein the DT-IL3 is a recombinantly expressed protein.

Embodiment 36. The method or DT-TL3 for the use of embodiment 35, wherein the DT-TL3 is obtained by recombinant expression in *Escherichia coli.*

Embodiment 37. The method of embodiment 35 or 36, or the DT-TL3 for the use according to embodiment 35 or 36, wherein the DT-IL3 comprises the catalytic and translocation domains of diphtheria toxin conjugated to human IL-3.

Embodiment 38. The method of embodiment 37, or the DT-IL3 for the use according to embodiment 37, wherein the catalytic and translocation domains of the diphtheria toxin are conjugated to the human IL-3 via a peptide or a chemical linker.

Embodiment 39. The method of any one of embodiments 1, 3-24, 26-29, or 31-38, or the DT-IL3 for the use according to any one of embodiments 2-23, 25-28, or 30-38, further comprising administering to the subject a therapeutic agent selected from the list comprising: Prednisone, Hydroxychloroquine, Chloroquine, Belimumab, Anifrolumab, Abatacept, Atacicept, LUPUZOR™ (rigerimod), Rituximab, Voclosporin, Aldesleukin, Baricitinib, BIIB059, BI655064, Bortezomib, BT063, Cenerimod, Dapirolizumab pegol, Edratide, Filgotinib, GS-9876, Iberdomide, IFN-α kinoid, Iguratimod, Nelfinavir, Obinutuzumab, OMS721, Rapamycin, RC18, RSLV-132, SM101, Theralizumab, Ustekinumab, Vobarilizumab, XmAb5871, Blisibimod, Tabalumab, Epratuzumab, Rigerimod, Tacrolimus, Rontalizumab, Sifalimumab, Anifrolumab, Tocilizumab, Infliximab, Metelimumab, Fresolimumab, Rilonacept, Cyclophosphamide, Methotrexate, Nintedanib, JBT-101, Imatinib, Pirfenidone, Nilotinib, Dasatinib, SAR100842, BMS-986202, BAY41-2272, Riociguat, Resunab, Ixekizumab, Brodalumab, Tralokinumab, Etanercept, Adalimumab, Ustekinumab, Golimumab, Secukinumab, Tildrakizumab, Tofacitinib, and Guselkumab.

Embodiment 40. The method of any one of embodiments 1 or 3, or the DT-IL3 for the use according to any one of embodiments 2 or 3, wherein the number of pDCs in the subject is reduced by about 20% to about 95%.

Embodiment 41. The method of embodiment 40, or the DT-IL3 for the use according to embodiment 38, wherein the reduction in the number of pDCs in the subject is dose-dependent.

Embodiment 42. A method of using modulation in the number of plasmacytoid dendritic cells (pDCs) as an indicator for continuing treatment of an autoimmune disease in a subject with a human interleukin-3 (IL-3)-diphtheria toxin conjugate (DT-IL3), the method comprising: determining the number of pDCs in a peripheral blood mononuclear cell sample and/or skin biopsy from the subject who has been administered DT-IL3, wherein about 20% or more reduction in the number of pDCs in the peripheral blood mononuclear cell sample and/or skin biopsy, in response to the administration of DT-IL3, is an indicator for the continuing treatment of the subject.

Embodiment 43. A human interleukin-3 (IL-3)-diphtheria toxin conjugate (DT-IL3) for use in a method of using modulation in the number of plasmacytoid dendritic cells (pDCs) as an indicator for continuing treatment of an autoimmune disease in a subject with DT-TL3, the method comprising: determining the number of pDCs in a peripheral blood mononuclear cell sample and/or skin biopsy from the subject who has been administered DT-TL3, wherein about 20% or more reduction in the number of pDCs in the peripheral blood mononuclear cell sample and/or skin biopsy, in response to the administration of DT-IL3, is an indicator for the continuing treatment of the subject.

Embodiment 44. The method of embodiment 42, or the DT-IL3 for the use according to embodiment 43, wherein the determination of pDC number comprises immunohisto-chemistry or immunofluorescence of a skin lesion biopsy.

Embodiment 45. The method of embodiment 42, or the DT-IL3 for the use according to embodiment 43, wherein the determination of pDC number comprises: a) isolation of peripheral blood mononuclear cells from a blood sample obtained from the subject using Ficoll-Paque® density gradient; and b) quantification of pDCs by flow cytometry using antibodies directed to CD14, CD3, BDCA4, and CD123, wherein the pDC population is identified as CD14–, CD3–, BDCA4+, CD123+.

EQUIVALENTS

The present invention is not to be limited in scope by the specific embodiments described which are intended as single illustrations of individual aspects of the invention, and functionally equivalent methods and components are within the scope of the invention. Indeed, various modifications of the invention, in addition to those shown and described herein, will become apparent to those skilled in the art from the foregoing description and accompanying drawings using no more than routine experimentation. Such modifications and equivalents are intended to fall within the scope of the appended claims.

INCORPORATION BY REFERENCE

All publications, patents and patent applications mentioned in this specification are herein incorporated by reference into the specification to the same extent as if each individual publication, patent, or patent application was specifically and individually indicated to be incorporated herein by reference.

Citation or discussion of a reference herein shall not be construed as an admission that such is prior art to the present invention.

What is claimed is:

1. A method of treating an autoimmune disease in a human subject, the method comprising reducing the number of plasmacytoid dendritic cells (pDCs) in the subject by administering a therapeutically effective dose of a human interleukin-3 (IL-3)-diphtheria toxin conjugate (DT-IL3) to the human subject, wherein the DT-IL3 comprises diphtheria toxin (DT) and interleukin-3 protein (IL-3), linked via a linker molecule, wherein:

(a) the DT comprises an amino acid sequence having a sequence at least 98% identical to the amino acid sequence of SEQ ID NO:3, wherein the amino acid sequence at least 98% identical to the amino acid sequence of SEQ ID NO: 3 comprises at least two domains of DT comprising:

(i) a catalytic domain comprising the sequence of amino acids 26-112 of SEQ ID NO: 1; and (ii) a translocation domain comprising amino acids 225-404 of SEQ ID NO:1, and (b) the IL-3 comprises an amino acid sequence having a sequence at least 95% identical to a mature IL-3 amino acid sequence having the amino acid sequence of SEQ ID NO: 2 without a signal peptide;

wherein the human subject prior to treatment has an elevated expression of at least one type I IFN-inducible gene in the skin or peripheral blood as compared to a healthy human subject; and wherein the treatment reduces the level of at least one cytokine or chemokine selected from chemokine ligand 4 (CXCL4), CXCL9, CXCL10, one or more type I interferons (type I IFNs), interleukin-6 (IL-6), tumor necrosis factor alpha (TNF-α), IL-8, regulated upon activation normal T cell expressed and presumably secreted (RANTES), macrophage inflammatory protein 1α (MIP1α), MIP1β, and monocyte chemoattractant protein-1 (MCP1) in the human subject.

2. The method of claim 1, wherein the reduction in the number of pDCs is accomplished through killing of pDCs by the administered DT-IL3 without affecting the number of T cells or B cells in the human subject by more than 15% as compared to the number of T cells or B cells in the human subject before administration of DT-IL3.

3. The method of claim 1, wherein the autoimmune disease is selected from lupus, Sjogren's syndrome, inflammatory arthritis, systemic sclerosis (SSc), morphea, psoriasis, lichen planus, dermatomyositis, lichen sclerosus, cutaneous graft-versus-host disease (GVHD), adrenergic drug resistance, alopecia areata, ankylosing spondylitis, antiphospholipid syndrome, autoimmune Addison's disease, autoimmune diseases of the adrenal gland, allergic encephalomyelitis, autoimmune hemolytic anemia, autoimmune hepatitis, autoimmune inflammatory eye disease, autoimmune neonatal thrombocytopenia, autoimmune neutropenia, autoimmune oophoritis, autoimmune orchitis, autoimmune thrombocytopenia, autoimmune thyroiditis, Behcet's disease, bullous pemphigoid, cardiomyopathy, cardiotomy syndrome, celiac sprue-dermatitis, chronic active hepatitis, chronic fatigue immune dysfunction syndrome (CFIDS), chronic inflammatory demyelinating polyneuropathy, Churg-Strauss syndrome, cicatricial pemphigoid, CREST syndrome, cold agglutinin disease, Crohn's disease, dense deposit disease, essential mixed cryoglobulinemia, fibro-myalgia-fibromyositis, glomerulonephritis, gluten-sensitive enteropathy, Goodpasture's syndrome, Graves' disease, Guillain-Barre, hyperthyroidism, idiopathic pulmonary fibrosis, idiopathic Addison's disease, idiopathic thrombo-cytopenia purpura (ITP), IgA neuropathy, juvenile arthritis, Ménière's disease, mixed connective tissue disease, multiple sclerosis, Myasthenia Gravis, myocarditis, type 1 diabetes mellitus, neuritis, endocrine gland failure, pemphigus vul-garis, pernicious anemia, polyarteritis nodosa, polychondri-tis, polyendocrinopathies, polyglandular syndromes, poly-myalgia rheumatica, polymyositis, post-myocardial infarction (post-MI), primary agammaglobulinemia, pri-mary biliary cirrhosis, psoriatic arthritis, Raynaud's phe-nomenon, relapsing polychondritis, Reiter's syndrome, rheumatic heart disease, rheumatoid arthritis, sarcoidosis, stiff-man syndrome, takayasu arteritis, temporal arteritis/ giant cell arteritis, ulcerative colitis, urticaria, uveitis, Uveitis Ophthalmia, vasculitides, vitiligo, and Wegener's granulomatosis.

4. The method of claim 1, wherein the type I IFN-inducible gene is selected from IFI27, IFI30, IFI6, IRF1, IFITM1, IFITM2, IFIT1, CXCL9, CXCL10, RSAD2, IFI44, IFI44L, IFI6, GBP1, MxB, SERPING1, LY6E, XAF3, IFIT2, IFIT3, MxA, and IRF7.

5. The method of claim 3, wherein the human subject exhibits elevated levels of one or more type I interferons compared to healthy individuals.

6. The method of claim 1, wherein the reduction in the number of pDCs results in reduced levels of at least one type I IFN-inducible gene as compared to levels of the at least one type I IFN-inducible gene in the human subject before administration of DT-IL3.

7. The method of claim 1, wherein the therapeutically effective dose of DT-IL3 is in the range of 1 µg/kg to 100 µg/kg.

8. The method of claim 7, wherein the administering of the therapeutically effective dose of DT-IL3 is repeated by administering the DT-IL3 for treatment cycles of 1 week, 2 weeks, 3 weeks, 4 weeks, 5 weeks, 6 weeks, 7 weeks, or 8 weeks.

9. The method of claim 8, wherein the administering of the therapeutically effective dose of DT-IL3 is repeated by administering the DT-IL3 at 1, 2, 3, 4, or 5 times per treatment cycle.

10. The method of claim 9, wherein the administering of the therapeutically effective dose of DT-IL3 is once daily for 1 day per treatment cycle, or once daily for 2, 3, 4, or 5 consecutive days per treatment cycle.

11. The method of claim 7, wherein the administration of the therapeutically effective dose of DT-IL3 does not affect the number of T cells or B cells in the subject.

12. The method of claim 1, wherein the number of pDCs in the human subject after administration of DT-IL3 is reduced by about 20% to about 95% as compared to the number of pDCs in the human subject before administration of DT-IL3.

13. The method of claim 1, wherein the type I interferon is IFN-α.

14. The method of claim 1, wherein the DT comprises an amino acid sequence at least 99% identical to the amino acid sequence of SEQ ID NO:3, and wherein IL-3 comprises an amino acid sequence at least 95% identical to the amino acid sequence of SEQ ID NO:2 without the signal peptide.

15. The method of claim 9, wherein the treatment cycle of 1, 2, 3, 4, 5, 6, 7, or 8 weeks is repeated 1, 2, 3, 4, 5 or more times.

16. The method of claim 14, wherein the DT comprises the amino acid sequence of SEQ ID NO:3, and wherein IL-3 comprises the amino acid sequence of SEQ ID NO:2 without the signal peptide.

* * * * *